(12) United States Patent
Ogino et al.

(10) Patent No.: US 10,347,035 B2
(45) Date of Patent: *Jul. 9, 2019

(54) DIAGNOSTIC IMAGE GENERATION APPARATUS AND DIAGNOSTIC IMAGE GENERATION METHOD

(71) Applicant: HITACHI, LTD., Tokyo (JP)

(72) Inventors: Masahiro Ogino, Tokyo (JP); Yoshimi Noguchi, Tokyo (JP); Takuma Shibahara, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/610,895

(22) Filed: Jun. 1, 2017

(65) Prior Publication Data
US 2017/0270706 A1 Sep. 21, 2017

Related U.S. Application Data

(63) Continuation of application No. 14/637,675, filed on Mar. 4, 2015, now Pat. No. 9,761,041.

(30) Foreign Application Priority Data

Mar. 28, 2014 (JP) ................................ 2014-068619

(51) Int. Cl.
*G06T 15/08* (2011.01)
*A61B 8/08* (2006.01)
(Continued)

(52) U.S. Cl.
CPC ............ *G06T 15/08* (2013.01); *A61B 8/0866* (2013.01); *A61B 8/13* (2013.01); *A61B 8/469* (2013.01);
(Continued)

(58) Field of Classification Search
None
See application file for complete search history.

(56) References Cited

U.S. PATENT DOCUMENTS

| | | | |
|---|---|---|---|
| 2006/0058605 | A1 | 3/2006 | Deischinger et al. |
| 2011/0091086 | A1 | 4/2011 | Seko et al. |
| 2014/0219524 | A1 | 8/2014 | Takeguchi |

FOREIGN PATENT DOCUMENTS

| | | |
|---|---|---|
| JP | 2011-083439 A | 4/2011 |
| JP | 2012-10965 A | 1/2012 |

OTHER PUBLICATIONS

Extended European Search Report received in corresponding European Application No. 15157444.9 dated Aug. 20, 2015.
(Continued)

*Primary Examiner* — Yi Wang
(74) *Attorney, Agent, or Firm* — Mattingly & Malur, PC

(57) ABSTRACT

A three-dimensional region of interest (ROI) is established with a high degree of accuracy, by a simple method without increasing a burden on the operator, in generating a three-dimensional projected image from medical volume data according to rendering, achieving more efficient interpretation of three-dimensional image and streamlining of diagnostic flow, with the use of the diagnostic image generation apparatus. An energy map is generated on a predetermined tomographic plane, assuming a preset start point as a reference and searching for a path that minimizes the energy, and then the path is set as a boundary of the three-dimensional ROI. The start point may be decided on the basis of the boundary inputted by a user, or the user may set the start point. The user may be allowed to adjust the boundary having been set. The boundary may also be determined on another plane orthogonal to the predetermined tomographic plane.

6 Claims, 26 Drawing Sheets

(51) Int. Cl.
| | |
|---|---|
| *A61B 8/00* | (2006.01) |
| *G06T 19/00* | (2011.01) |
| *A61B 8/13* | (2006.01) |
| *G06T 3/40* | (2006.01) |
| *G06T 7/12* | (2017.01) |
| *G06T 7/181* | (2017.01) |

(52) U.S. Cl.
CPC .............. *A61B 8/5207* (2013.01); *G06T 3/40* (2013.01); *G06T 7/12* (2017.01); *G06T 7/181* (2017.01); *G06T 19/00* (2013.01); *A61B 8/466* (2013.01); *A61B 8/483* (2013.01); *G06T 2207/10012* (2013.01); *G06T 2207/10076* (2013.01); *G06T 2207/10136* (2013.01); *G06T 2207/20101* (2013.01); *G06T 2207/20104* (2013.01); *G06T 2207/30044* (2013.01); *G06T 2210/41* (2013.01); *G06T 2219/008* (2013.01)

(56) References Cited

OTHER PUBLICATIONS

Mortensen, E. et al., "Adaptive Boundary Detection Using "Live-Wire" Two-Dimensional Dynamic Programming", Computers in Cardiology 1992, Oct. 11, 1992, pp. 635-638.

Communication Pursuant to Article 94(3) EPC received in corresponding European Application No. 15 157 444.9 dated Sep. 14, 2018.

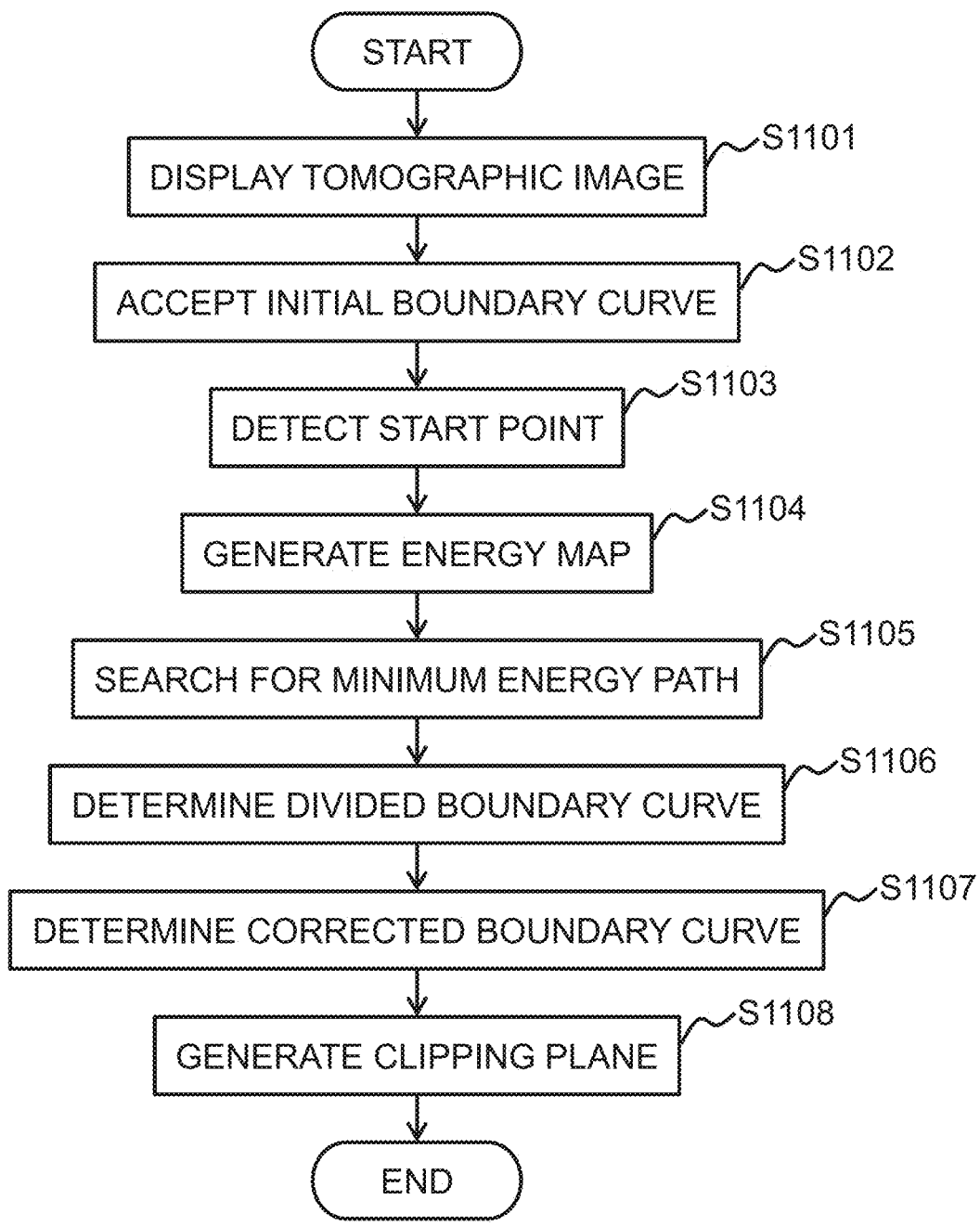

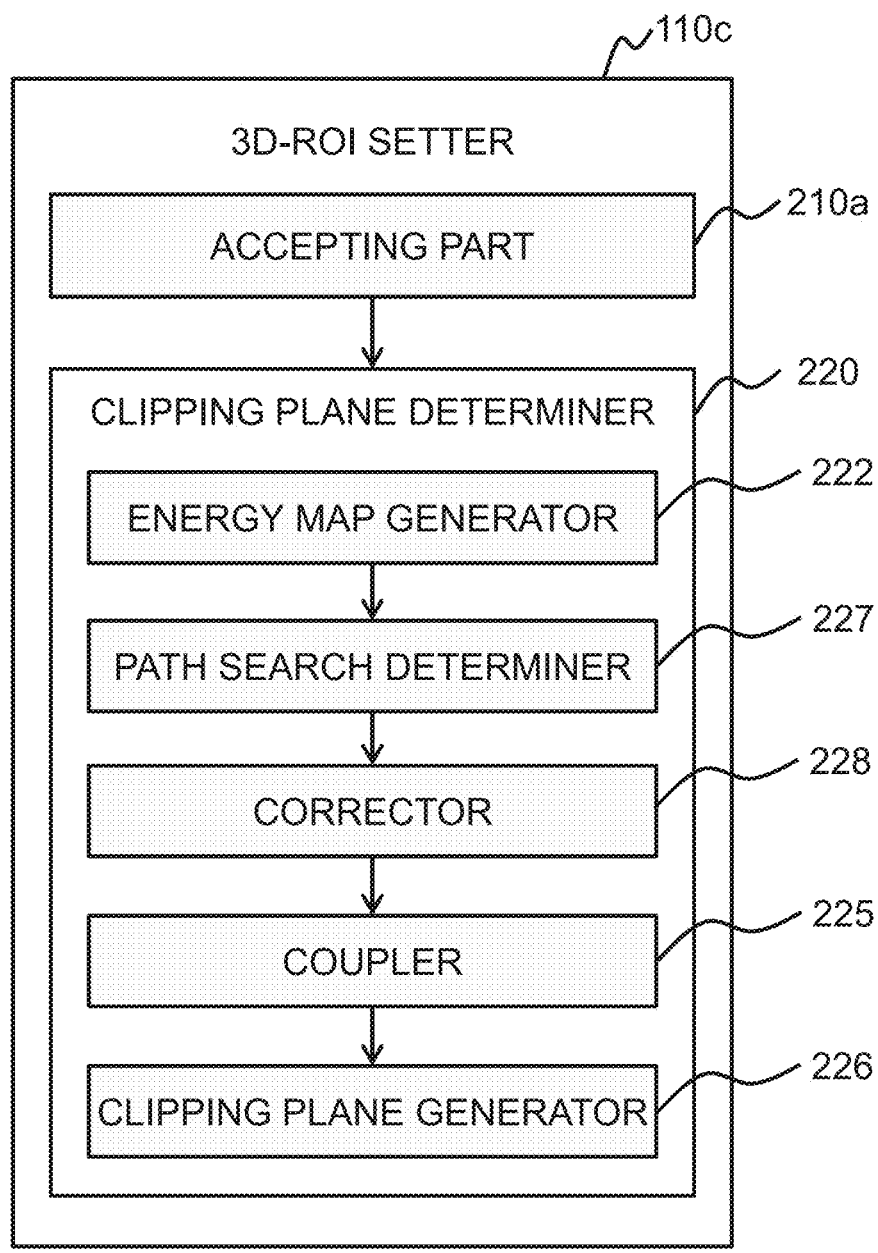

DIAGNOSTIC IMAGE GENERATION APPARATUS AND DIAGNOSTIC IMAGE GENERATION METHOD

INCORPORATION BY REFERENCE

The present application is a continuation application of U.S. Ser. No. 14/637,675, filed Mar. 4, 2015 which claims priority from Japanese patent application JP-2014-0068619 filed on Mar. 28, 2014, the content of which is hereby incorporated by reference into this application.

FIELD OF THE INVENTION

The present invention relates to a technique for generating a three-dimensional projected image in a diagnostic image generation apparatus, and more particularly, it relates to a technique for establishing in volume data being acquired, a three-dimensional region of interest (ROI) to which a rendering process is applied.

DESCRIPTION OF THE RELATED ART

A diagnostic image generation apparatus, including an ultrasound diagnostic apparatus, for acquiring a medical image, is required to generate a two-dimensional image (projected image) from acquired three-dimensional image data (medical volume data), and visualize an image of tissue that is targeted for imaging. For this purpose, such apparatus is equipped with a function of generating a three-dimensional projected image by volume rendering, and a function of displaying thus generated image. In generating the three-dimensional projected image, a range to which the rendering process is applied is configured as a three-dimensional region of interest (hereinafter, referred to as "three-dimensional ROI"). If the tissue to be imaged has a complicated shape such as a fetus, for instance, it is necessary to establish the three-dimensional ROI as accurate as possible. Otherwise, in the image being obtained, other tissue not to be imaged, such as floating substance in amniotic fluid and placenta, may hide the tissue to be imaged, and this may act as an impediment to observation. However, since the shape of the tissue to be imaged is complicated, extremely cumbersome operation is needed in setting the three-dimensional ROI accurately.

In order to solve this problem, there is a technique that an operator is made to designate a region to be imaged, e.g., outline points of the fetus, so as to detect a contour of the region to be imaged that is based on the outline points, and then assume this contour as a boundary of the three-dimensional ROI, thereby establishing the three-dimensional ROI (see Japanese Unexamined Patent Application Publication No. 2012-010965, hereinafter, referred to as "patent document 1").

DESCRIPTION OF THE RELATED ART

In the method of the patent document 1, upon acceptance of designation of one point, brightness information (magnitude of brightness) about the environment of the designated point is used to specify the contour. However, in actual volume data, it is likely to be difficult to make a distinction according to the brightness value, between a region to be imaged and a region not imaged. Therefore, this method may fail to accurately extract the tissue to be imaged and establish the three-dimensional ROI.

The present invention has been made in view of the situation above, and the present invention provides a technique to support establishing a desired three-dimensional ROI with a high degree of accuracy, by a simple method without increasing burden on the operator, in generating a three-dimensional projected image from medical volume data according to rendering, achieving more efficient interpretation of 3D image and streamlining of diagnostic flow, with the use of the diagnostic image generation apparatus.

SUMMARY OF THE INVENTION

In the present invention, an energy map is generated on a predetermined tomographic plane, assuming a preset start point as a reference and searching for a path that minimizes the energy, and then, the path is set as a boundary of the three-dimensional ROI. The start point may be decided on the basis of the boundary inputted by a user, or the user may set the start point. The user may be allowed to adjust the boundary having been set. The boundary may be determined further on the plane being orthogonal to the predetermined tomographic plane according to a similar method.

Specifically, a diagnostic image generation apparatus is provided, including a three-dimensional ROI setter configured to establish a three-dimensional ROI to which a rendering process is applied, on volume data being an aggregate of data acquired from three-dimensional space within a living body, and a projected image generator configured to execute the rendering process by using the data within the three-dimensional ROI, so as to generate a three-dimensional projected image, the three-dimensional ROI setter including, an accepting part configured to accept an instruction from a user, on a predetermined tomographic image of the volume data, and a clipping plane determiner configured to determine a clipping plane that spatially separates tissue to be imaged and tissue not imaged in the three-dimensional ROI, and the clipping plane determiner determines a boundary curve on the tomographic image, the boundary curve passing a start point that is specified by the instruction, and connecting pixels that minimize a sum of energy values obtained by reflecting a brightness value of one pixel to a brightness value of an adjacent pixel, and determines the clipping plane from the boundary curve.

In addition, a diagnostic image generation method is provided with an accepting step that accepts an instruction from a user on a predetermined tomographic image of the volume data being an aggregate of data acquired from three-dimensional space within a living body, and a clipping plane determining step that determines a clipping plane to spatially separate tissue to be imaged and tissue not imaged in the three-dimensional ROI in which the volume data is subjected to the rendering process, and a projected image generation step that executes the rendering process on the volume data in the three-dimensional ROI specified by the clipping plane, and the clipping plane determining step determines a boundary curve on the tomographic image, the boundary curve passing a start point specified by the instruction, and connecting pixels that minimize a sum of energy values obtained by reflecting a brightness value of one pixel to a brightness value of an adjacent pixel, and determines the clipping plane from the boundary curve.

According to the present invention, in generating a three-dimensional projected image by rendering, from medical volume data, it is possible to support establishing of a desired three-dimensional ROI by a simple method with a high degree of accuracy, without increasing burden on the operator, thereby achieving more efficient interpretation of 3D image and streamlining of diagnostic flow, with the use of the diagnostic image generation apparatus.

BRIEF DESCRIPTION OF THE DRAWINGS

FIG. 15 is a flowchart showing the 3D-ROI setting process of the first embodiment;

FIG. 21 is a functional block diagram showing the 3D-ROI setter according to the third embodiment;

DESCRIPTION OF THE PREFERRED EMBODIMENTS

<<First Embodiment>>

The first embodiment to which the present invention is applied will be explained. Here, an ultrasound image-capturing apparatus will be taken as an example to explain the diagnostic image generation apparatus. A fetus is assumed as the tissue to be imaged. Therefore, floating substance in amniotic fluid, placenta, and the like, may be the tissue not imaged.

[Configuration of the Ultrasound Image-Capturing Apparatus]

Figure 1:
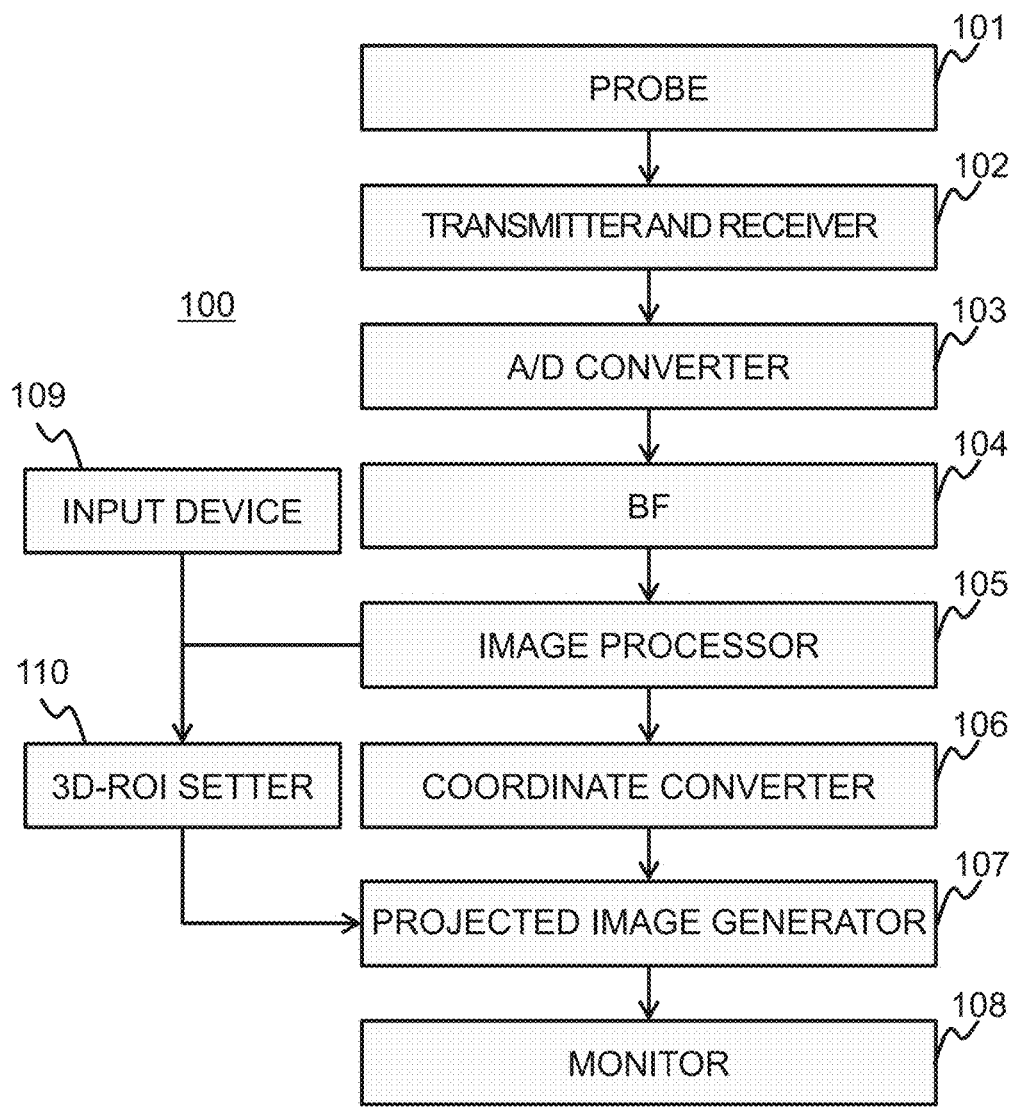
FIG. 1 is a functional block diagram showing the ultrasound image-capturing apparatus (diagnostic image generation apparatus) of the first embodiment.

FIG. 1 is a functional block diagram showing the ultrasound image-capturing apparatus (diagnostic image generation apparatus) according to the present embodiment. As illustrated, the ultrasound image-capturing apparatus 100 of the present embodiment is provided with a probe 101 with ultrasonic transducers configured to acquire three-dimensional echo data, a transmitter and receiver 102 configured to control a transmit pulse and amplify a received echo, an analogue/digital converter (analogue/digital converting means; A/D) 103 configured to digitalize the received echo signal being amplified, a beamforming (BF) processor (BF processing means) 104 configured to bind (perform beamforming of) the received echoes from many transducers, an image processor (image processing means) 105, a coordinate converter (coordinate converting means) 106, a projected image generator (projected image generating means) 107, a monitor (display means) 108, an input device (input means) 109, and a three-dimensional ROI setter (3D ROI setting means) 110.

The image processor 105 subjects RF signals from the BF processor 104 to image processing, and generates tomographic image data (hereinafter, simply referred to as "tomographic image"). The image processing here includes, dynamic range compression, filtering, scan conversion process, and the like. The monitor 108 displays the tomographic image generated by the image processor 105.

The coordinate converter 106 subjects the tomographic image to orthogonal coordinate conversion, thereby generating volume data.

The three-dimensional ROI setter 110 establishes on the volume data, the three-dimensional region of interest (3D-ROI) to which the rendering process is applied. The 3D-ROI of the present embodiment has a clipping plane that spatially separates the tissue to be imaged from the tissue not imaged. As described above, the clipping plane serves as a surface where the rendering process is started. In the present embodiment, a boundary curve is set on a predetermined tomographic image, being a line intersection of the tomographic image and the clipping plane, thereby determining the clipping plane.

The projected image generator 107 executes the rendering process to the data within the 3D-ROI out of the volume data, and generates a three-dimensional projected image.

The monitor 108 displays the tomographic image generated by the image processor 105, the projected image generated by the projected image generator 107, and the like. By way of example, the monitor is further provided with a touch panel to accept an input from the user. The touch panel is made up of plural touch sensors, arranged on the display surface of the monitor 108.

The input device 109 may be made up of, for example, the touch panel, a keyboard, a trackball, and the like, serving as a user interface to accept various inputs from the user.

The probe 101 is only required to acquire 3D data, and any probe system is applicable, such as a free-hand system, a mechanical scanning system, and 2D-array probe system.

In an information processor incorporating a CPU and a memory, the CPU loads in the memory, programs being held in advance in a storage device and executes those programs, thereby implementing the image processor 105, the coordinate converter 106, the projected image generator 107, and the three-dimensional ROI setter 110.

[Three-dimensional ROI Setter]

The three-dimensional ROI setter 110 of the present embodiment establishes the 3D-ROI to which the rendering process is applied, on the volume data being an aggregate of data that is acquired from the three-dimensional space within a living body.

The three-dimensional ROI setter 110 of the present embodiment accepts an input of the boundary curve from the user, on a predetermined tomographic image. The boundary curve is a line intersection between the clipping plane and the tomographic image, as described above. Then, the accepted boundary curve is corrected, and a corrected boundary curve is obtained. The corrected boundary curve is three-dimensionally expanded to obtain the clipping plane, and the 3D-ROI is established.

In the present embodiment, a curve (spline curve) is accepted as the boundary curve. A reason why the spline curve is accepted as the boundary curve and a reason why correction is necessary will be described in the following, prior to explaining the processing of each part. Here, the explanation will be provided, taking as an example that a fetus is assumed as the imaging target (tissue to be imaged).

Figure 2:
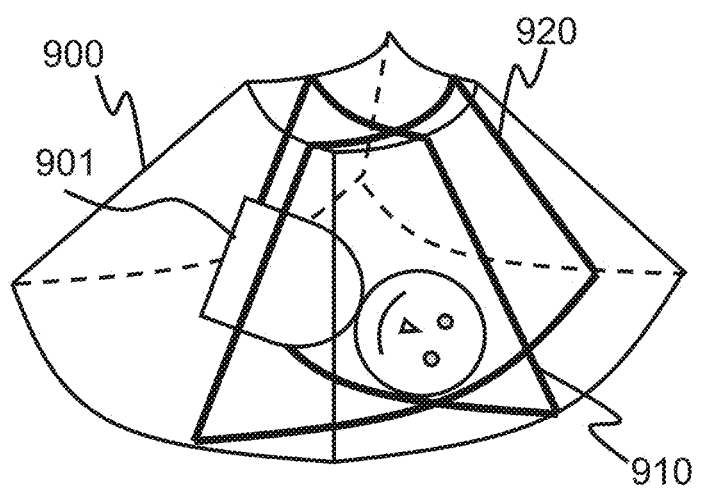
FIG. 2 illustrates one example of volume data that is obtained according to three-dimensional scanning by the diagnostic image generation apparatus.

Firstly, taking an image of fetus as an example, a conventional 3D-ROI setting process will be explained. FIG. 2 illustrates the volume data 900 that is obtained by three-dimensional scanning in the ultrasound image-capturing apparatus 100. In this example here, a plane parallel to the tomographic plane 910 including a body axis of the fetus 901 is referred to as axial plane, and the tomographic plane 920 orthogonal to the body axis is referred to as sagittal plane. The axial plane 910 and the sagittal plane 920 are orthogonal to each other.

Figure 3A:
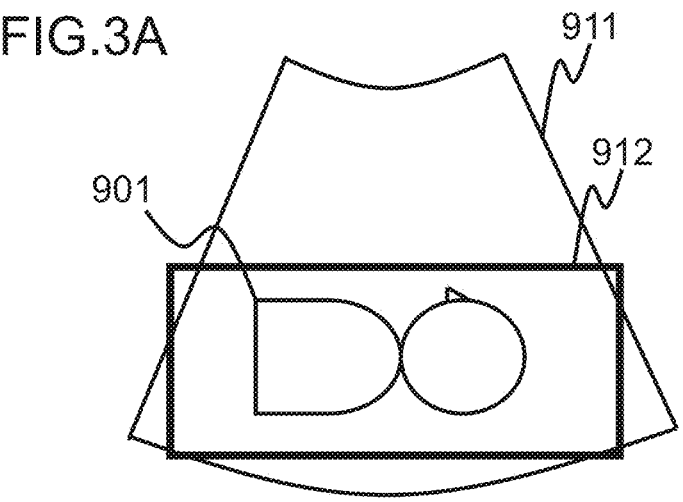
FIG. 3A illustrates a three-dimensional ROI (3D-ROI) on an axial plane of the diagnostic image generation apparatus.

A tomographic image of the axial plane 910 is referred to as axial image, and a tomographic image of the sagittal plane 920 is referred to as sagittal image. FIG. 3A illustrates the axial image 911, and FIG. 3B illustrates the sagittal image 921.

The 3D-ROI is a three-dimensional region, as the name indicates. Generally, in the image of the tomographic plane showing the fetus 901 most appropriately (basically, the axial image 911), there is set a line intersection with the 3D-ROI, and on the basis of the line intersection, the image is expanded three-dimensionally.

Figure 4:
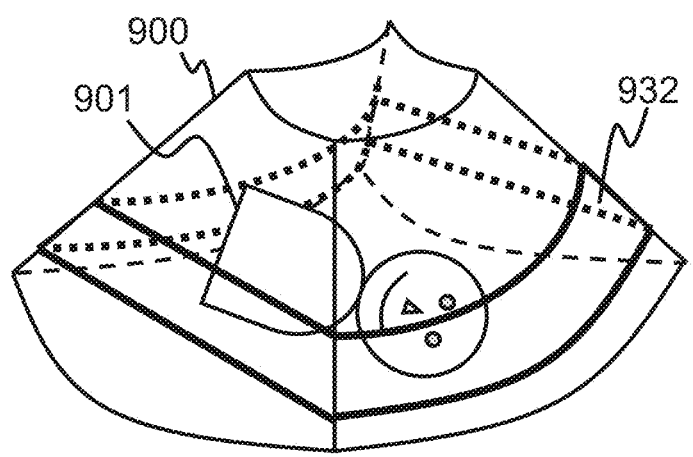
FIG. 4 illustrates the 3D-ROI of the diagnostic image generation apparatus.

As shown in FIG. 3A, in the axial image 911, the line intersection (axial ROI) 912 of the 3D-ROI and the axial image is set, and the 3D-ROI 932 as shown in FIG. 4 is determined. The 3D-ROI 932 is generated by copying the axial ROI 912 established on any axial plane, to all the other axial planes.

Figure 3B:
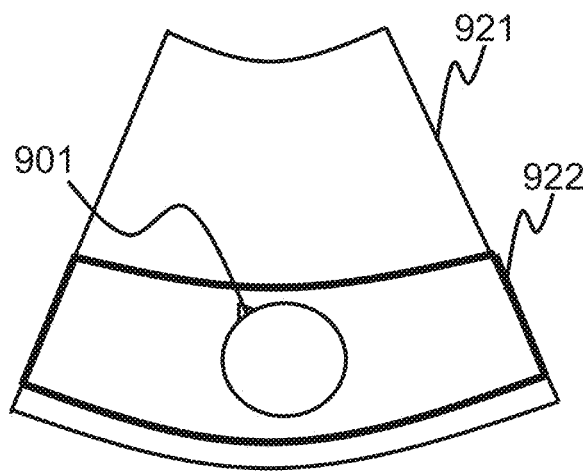
FIG. 3B illustrates the 3D-ROI on a sagittal plane of the diagnostic image generation apparatus.

As shown in FIG. 3B, in an arbitrary sagittal image 921, the 3D-ROI being generated corresponds to the region 922 with the height being the line intersection with the axial ROI 912, in parallel to the top and bottom sides of the sagittal image 921, entirely across the lateral direction of the sagittal image 921.

The 3D-ROI 932 is established and the rendering process is applied only to the volume data within this region, thereby reducing the amount of the rendering process and improving the real-time property. It is further possible to remove noise due to floating substances around the region of interest (ROI), multiple reflection, and the like. Therefore, setting of the 3D-ROI is an extremely important function in displaying the three-dimensional projected image.

Figure 5A:
FIG. 5A and FIG. 5B illustrate a method for setting the 3D-ROI in a conventional diagnostic image generation apparatus.

If the tissue to be imaged within the 3D-ROI has a complicated shape, like the fetus as shown in FIG. 5A, setting of the top side 942 of the axial ROI 912 in the figure is significant. Hereinafter, this top side is referred to as a boundary curve 942. In order to enhance the accuracy for extracting the tissue to be imaged, the boundary curve 942 is established using not the straight line as shown in FIG. 5A, but a spline curve 942 as shown in FIG. 5B.

Figure 5B:

As shown in FIG. 5B, the boundary curve 942 is established between the fetus and placenta. The shape of the amniotic fluid region between the fetus and the placenta is substantially a convex surface or a concave surface, according to an empirical rule. Therefore, by generating the boundary curve 942 with a spline curve, the 3D-ROI determined by this boundary curve achieves a smooth convex surface or concave surface. With this 3D-ROI, it is possible to obtain an appropriate three-dimensional projected image.

However, in actual clinical data, even though the boundary curve 942 is specified by the spline curve, it is difficult in many cases, to accurately draw a boundary in the amniotic fluid region between the placenta and the fetus. By way of example, in FIG. 6, if the rendering process is applied to the axial ROI 409 (3D-ROI) including the boundary curve 401 being established by the spline curve, the nose and the mouth of the fetus may be invisible.

Figure 6:
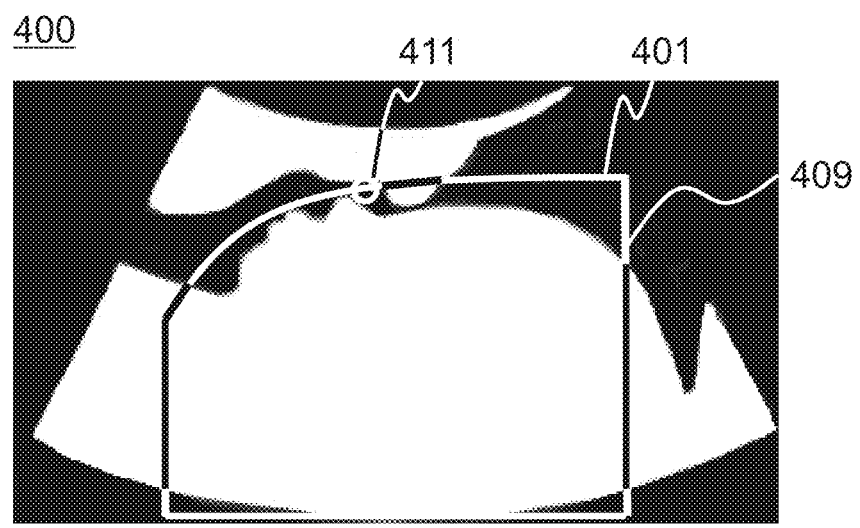
FIG. 6 illustrates the case where it is difficult to draw a boundary according to the conventional method, and further explains the process of the first embodiment.

In the present embodiment, for the case as shown in FIG. 6, the user corrects the boundary curve 401 established by the spline curve, and avoids inappropriate 3D-ROI setting. This aims at achieving greater functionality. Hereinafter, an explanation will be provided as to this three-dimensional ROI setter 110.

Figure 7:
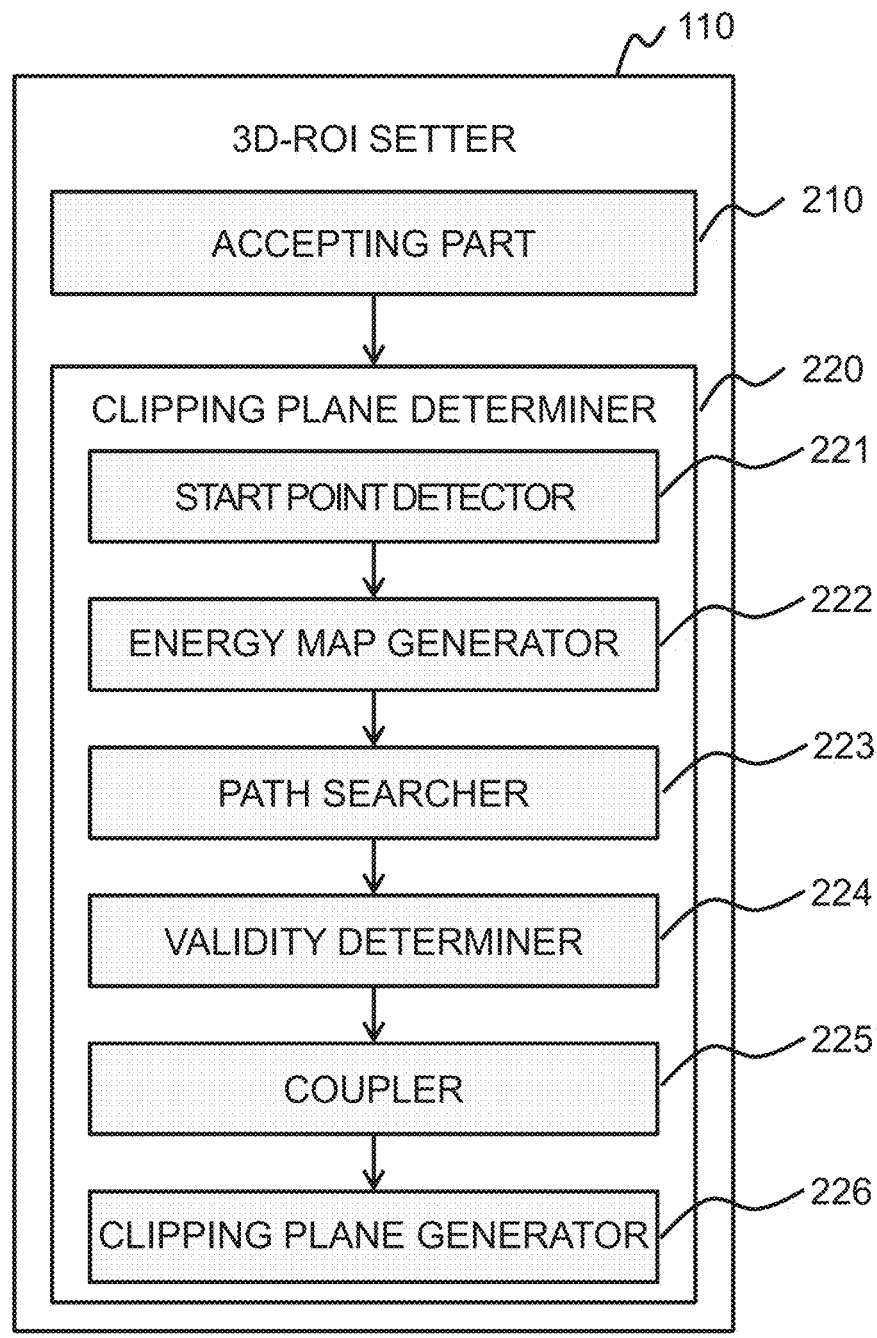
FIG. 7 is a functional block diagram showing the 3D-ROI setter of the first embodiment.

In order to achieve the aforementioned functionality, as shown in FIG. 7, the three-dimensional ROI setter 110 of the present embodiment is provided with, an accepting part (accepting means) 210 configured to accept an instruction from the user on a predetermined tomographic image, and a clipping plane determiner (clipping plane determining means) 220 configured to determine a clipping plane that spatially separates tissue to be imaged and tissue not imaged in a 3D-ROI, and the clipping plane determiner 220 determines a boundary curve on the tomographic image, the boundary curve passing through a start point specified according to the instruction, and connecting pixels that minimize a sum of energy values obtained by reflecting a brightness value of one pixel to a second brightness value of an adjacent pixel, and determines the clipping plane from the boundary curve.

The accepting part 210 of the present embodiment may accept as the instruction, the boundary curve (spline curve) which is the line intersection of the tomographic image (tomographic plane) and the clipping plane, being assumed as an initial boundary curve. Hereinafter, in the present embodiment, a predetermined tomographic plane is assumed as an axial plane, and a predetermined tomographic image is assumed as an axial image.

As shown in FIG. 6, in the present embodiment, the monitor 108 displays the axial image 400, and accepts the initial boundary curve 401 on this image. The axial image 400 being displayed is the tomographic image generated by the image processor 105. It is to be noted here that the touch panel provided on the monitor 108 may accept the initial boundary curve 401. The user inputs a curve that passes through the amniotic fluid region between the placenta and the fetus, for instance. The curve being inputted may be accepted as a spline curve.

The clipping plane determiner 220 of the present embodiment corrects the initial boundary curve, determines the corrected boundary curve and further determines the clipping plane. In order to achieve this, the clipping plane determiner 220 of the present embodiment is provided with a start point detector (start point detecting means) 221 configured to detect a start point on the initial boundary curve, an energy map generator (energy map generating means) 222 configured to divide the tomographic image into two by a line of pixels passing the start point, calculate an energy value of each pixel in each of the images being divided, and generate energy maps respectively, a path searcher (path searching means) 223 configured to search for a minimum energy path being a path connecting pixels, the path minimizing a sum of the pixel values in each of the energy maps, a validity determiner (validity determining means) 224 configured to determine a divided boundary curve in each of the divided images, in response to maximum distance between the initial boundary curve and the minimum energy path, a coupler (coupling means) 225 configured to couple the divided boundary curves, so as to obtain a boundary curve, and a clipping plane generator (clipping plane generating means) 226.

[Start Point Detector]

As shown in FIG. 6, the start point detector 221 detects as the start point 411, a point that is certainly conceived as in the amniotic fluid region (region not targeted for imaging) on the initial boundary curve 401. In the present embodiment, a pixel with the lowest brightness (a minimum brightness pixel) is detected as the start point 411 on the initial boundary curve 401 in the axial image 400. If there is more than one minimum brightness pixel, the pixel initially detected is assumed as the start point 411.

Generally, it is known that the brightness level of the amniotic fluid region is likely to be low, and it is assumed that at least one point on the initial boundary curve 401 set by a user (a doctor or a laboratory personnel) passes through the amniotic fluid region.

Upon detecting the start point 411 by the start point detector 221, it is further possible to provide a threshold processing. The threshold processing determines whether or not there exists a brightness value equal to or less than a predetermined threshold on the initial boundary curve 401. Only when there exists a pixel with the brightness value equal to or less than the predetermined threshold, the start point detecting process is executed. On the other hand, if there exists no pixel with the brightness value equal to or less than the predetermined threshold, the start point detecting process is terminated, and the 3D-ROI correcting process is also terminated. Then, an error message may be outputted together with the initial boundary curve (spline curve) 401 already established.

[Energy Map Generator]

The energy map generator 222 divides the tomographic image (axial image 400) into two, at the start point 411, and generates an energy map in each of the images (divided images).

Figure 8:
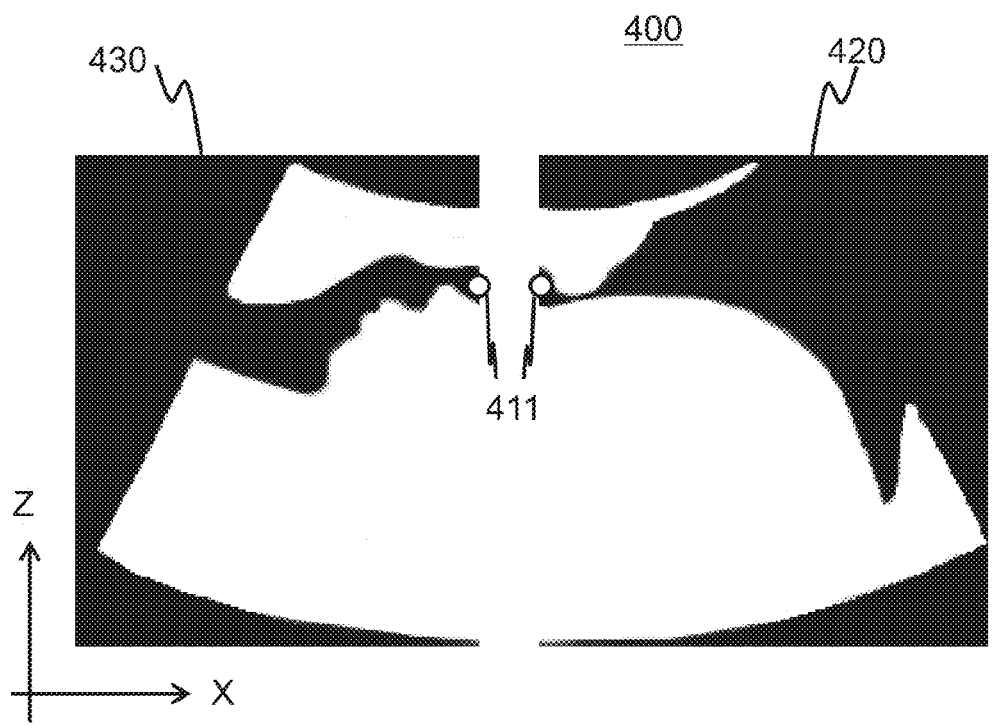
FIG. 8 illustrates an energy map generation process according to the first embodiment.
Figure 9:
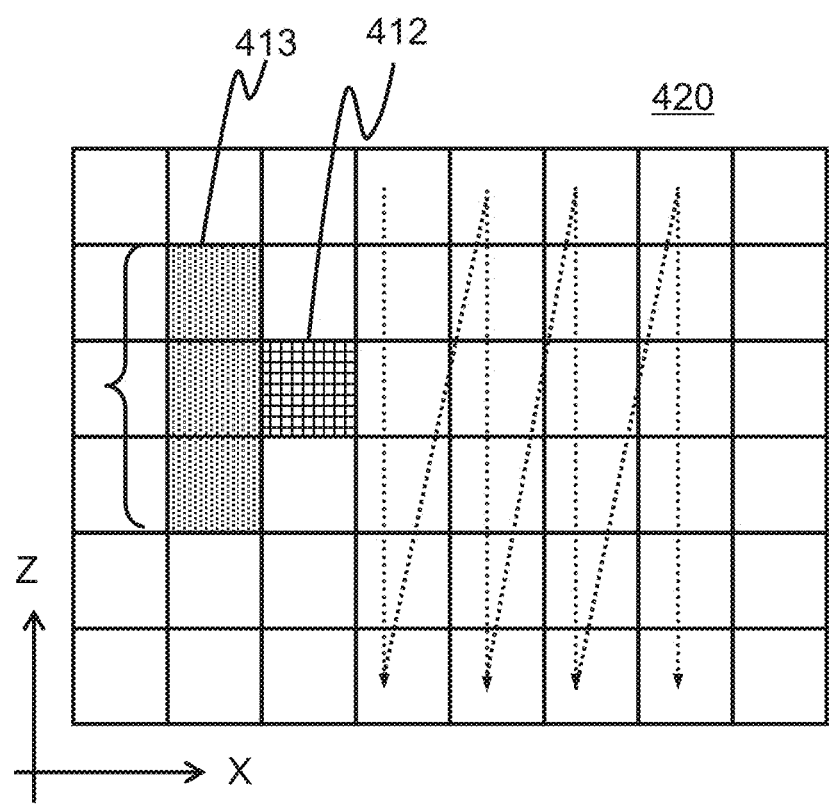
FIG. 9 illustrates the energy map generation process according to the first embodiment.
Figure 10:
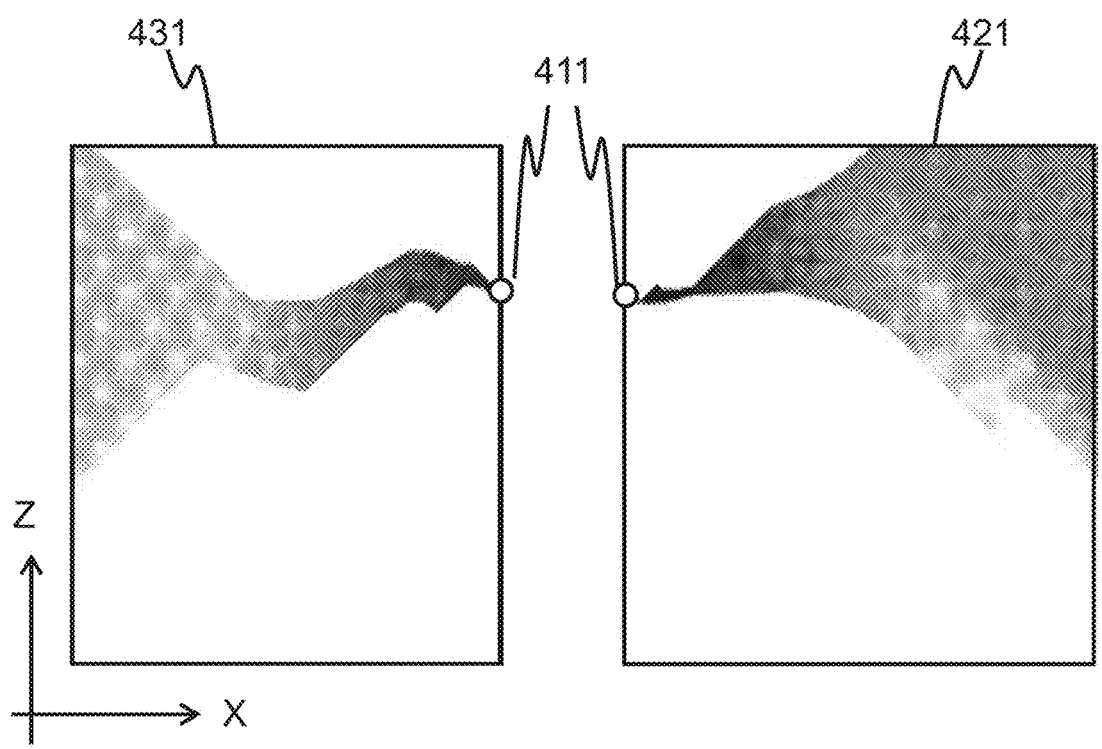
FIG. 10 illustrates the energy map that is generated according to the first embodiment.

With reference to FIG. 8, FIG. 9, and FIG. 10, the energy map generating process according to the energy map generator 222 will be explained. Hereinafter, for ease of explanation, the depth direction of the axial image 400 (traveling direction of ultrasound beams) is referred to as the z-direction, the direction orthogonal to the z-direction on the axial image 400 (left and right direction) is referred to as the x-direction.

The energy map generator 222 divides the axial image 400 into two in the x-direction, by the line (pixel line) in the z-direction passing the start point 411. The tomographic images (divided images) are labeled as 420 and 430, respectively. In the figure, using the divided image 420 on the right, the subsequent process will be explained.

As shown in FIG. 9, the energy map generator 222 adds a value of the pixel with the minimum brightness out of the three pixels 413, to the value of the pixel 412 targeted for the processing, the three pixels being adjacent to the targeted pixel 412 (left-adjacent pixel, upper-left adjacent pixel, and lower-left adjacent pixel) on the side opposite to the direction in which the energy map generation proceeds (positive x-direction). In the case where there are two or more pixels having the minimum brightness value within the adjacent three pixels, a pixel to be selected is defined in advance.

This addition process is applied to the two divided images 420 and 430 entirely, from the start point 411 side. Accordingly, the energy maps EM(i,j) 421 and 431 as shown in FIG. 10 are generated. It is to be noted that in thus obtained energy maps EM, the lower brightness has the region (pixels), the smaller is the energy.

The process to generate the energy maps EM(i,j) as described above is expressed by the following formula (1):

$$EM(i,j)=E(i,j)+\min(EM(i-1,j-1),EM(i-1,j),EM(i-1,j+1)) \quad (1)$$

Here, E(i,j) represents an energy value at the pixel position (i,j).

It is to be noted that a brightness value is used as the energy value in the present embodiment but this is not the only example. By way of example, gradient information of brightness, an edge amount, entropy, likelihood, HoG, SaliencyMap, L1 and L2 norms, and the like, or a combination thereof, may be utilized.

[Path Searcher]

The path searcher 223 searches for a path tracking the minimum energy value in the energy maps 421 and 431. The path searching is performed in each of the energy maps 421 and 431.

Figure 11:
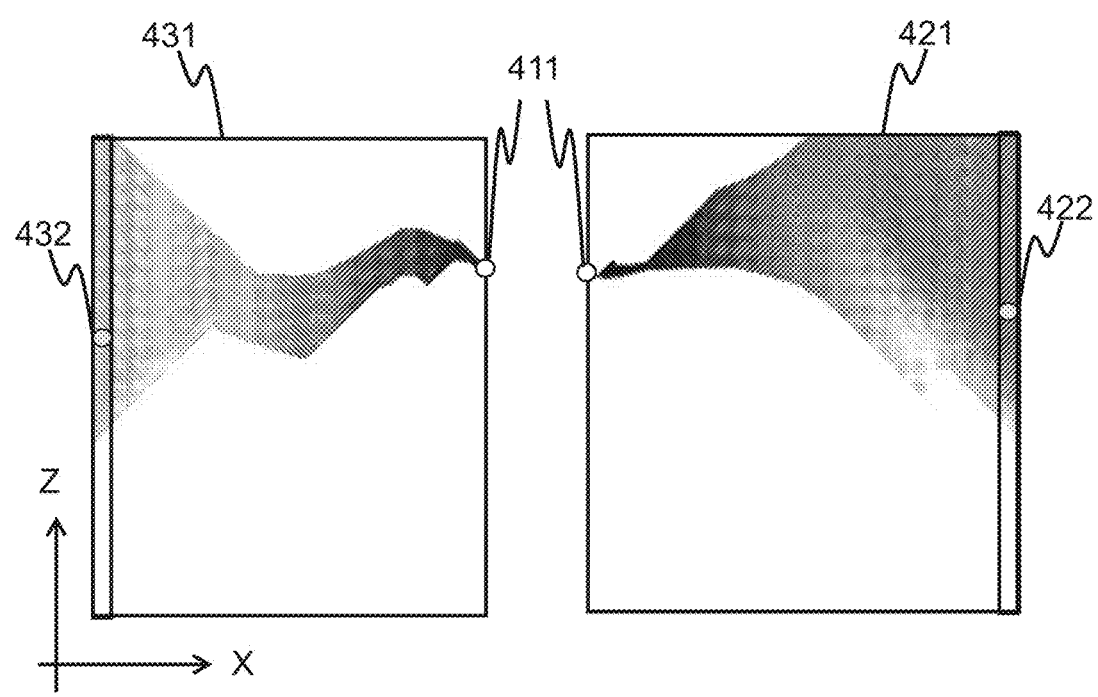
FIG. 11 illustrates a minimum energy path searching process of the first embodiment.
Figure 12:
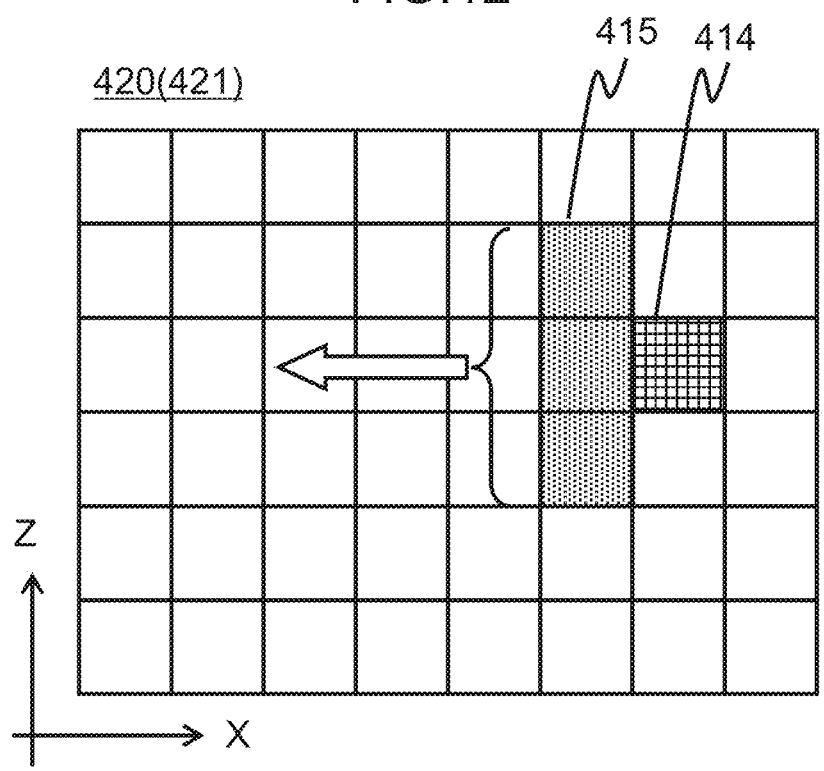
FIG. 12 illustrates the minimum energy path searching process of the first embodiment.

With reference to FIG. 11 and FIG. 12, the minimum energy path searching process according to the path searcher 223 will be explained. The path searcher 223 searches for the minimum energy path from the generated energy maps 421 and 431.

Specifically, searching is performed from the search start points 422 and 432 heading for the start point 411, and a path candidate is generated. The pixels with the minimum value at the respective opposite ends of the start point 411 are assumed as the search start points 422 and 432, in the respective energy maps 421 and 431 being generated. As shown in FIG. 11, in the energy map 421, searching is performed from the search point 422, whereas in the energy map 431, it is performed from the left end.

Using the divided image 420 (energy map 421), details of the searching will be explained. As shown in FIG. 12, when searching is performed, a pixel with the lowest energy value is selected out of the three pixels 415, and the selected pixel is assumed as the next current position pixel 414. The three pixels 415 are adjacent to the current position pixel 414 (left-adjacent pixel, upper-left adjacent pixel, and lower-left adjacent pixel) on the side (left side), in the direction in which the searching proceeds (negative x-direction). Then, thus selected current position pixels 414 are connected sequentially, thereby generating a minimum energy path that passes the start point 414.

In the minimum energy path searching process according to the path searcher 223, a subject to draw a boundary between placenta and fetus results in a question of a dynamic programming that solves the formula (2):

$$R_{min} = \underset{R_i}{\operatorname{argmin}} \sum_{i=1}^{m} EM(R_i) \qquad (2)$$

Here, $R_{min}$ represents a minimum energy path, $EM(R_i)$ represents a total energy value (energy additional value) of the path candidate i being searched for, and argminf(x) represents x that minimizes the function f(x). The image size of the axial image 400 is assumed as n pixels in the x-direction (horizontal direction), and m pixels in the z-direction (vertical direction) (here, n and m are integers at least one).

As described above, in the present embodiment, the additional value of energy is calculated as to each path candidate, and the path candidate i with the minimum additional value is assumed as the minimum energy path.

It is to be noted that in the present embodiment, the energy values of the surrounding three pixels are used for the judgment, both in generating the energy map and in searching for the minimum energy path, but it is a matter of course that this is not the only example.

[Validity Determiner]

The validity determiner 224 determines validity of the minimum energy path having been searched for, and if it is determined as valid, the path is assumed as a divided boundary curve after the correction. On the other hand, if it is determined as invalid, the initial boundary curve is assumed as the divided boundary curve after the correction.

The validity determination is made, for example, by determining whether or not maximum distance between the initial boundary curve set by the user and the minimum energy path being generated is equal to or larger than a threshold. The maximum distance therebetween is detected, and when the maximum distance is smaller than the threshold, it is determined that the path is valid, and when it is equal to or larger than the threshold, it is determined as invalid. In other words, the validity determiner 224 of the present embodiment assumes the initial boundary curve as the boundary curve, when the maximum distance between the initial boundary curve and the minimum energy path is equal to or larger than the predetermined distance threshold, whereas when the maximum distance is smaller than the distance threshold, the minimum energy path is assumed as the boundary curve.

Figure 13:
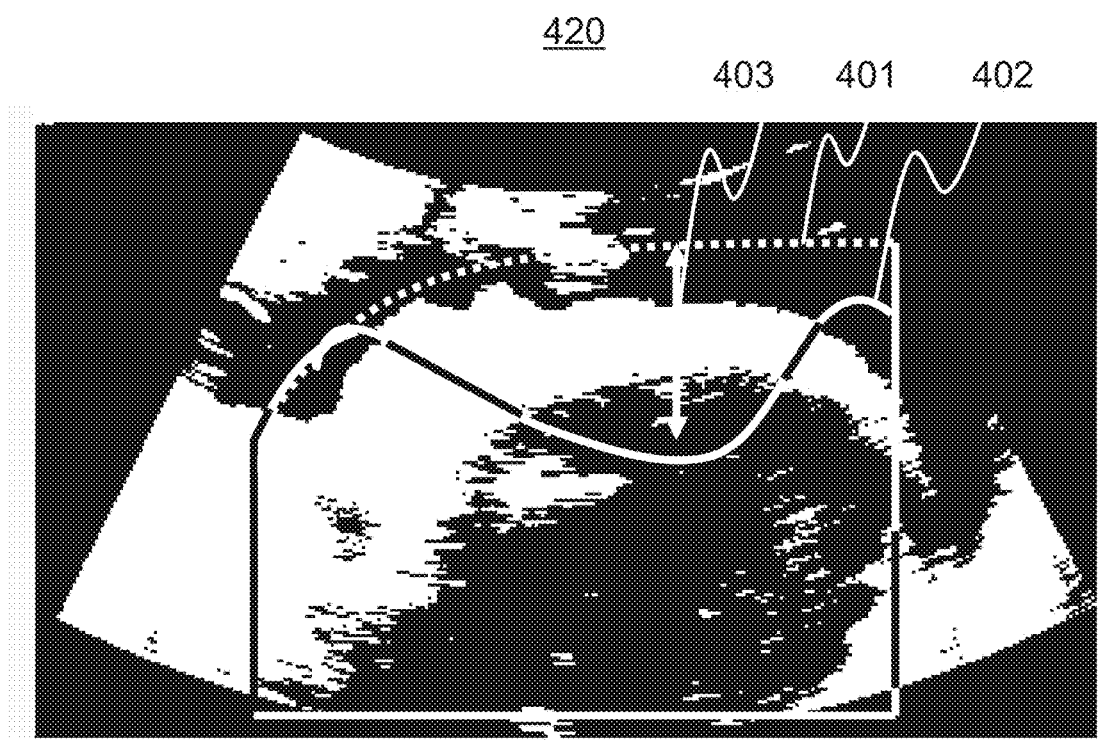
FIG. 13 illustrates a validity determination process of the first embodiment.

Byway of example, as shown in FIG. 13, when the maximum distance 403 between the initial boundary curve 401 and the minimum energy path 402 is equal to or larger than the threshold, the minimum energy path 402 being generated is not used, but the initial boundary curve 401 is used.

In the present embodiment, the maximum distance 403 between the initial boundary curve 401 and the minimum energy path 402 being generated is used as the information for determination, but this is not the only example. Byway of example, it is alternatively possible to employ a method for measuring a degree of similarity between the curves utilizing a variance, and the like, or the energy value itself may be used, so as to determine the validity of the minimum energy path being generated.

[Coupler]

Figure 14:
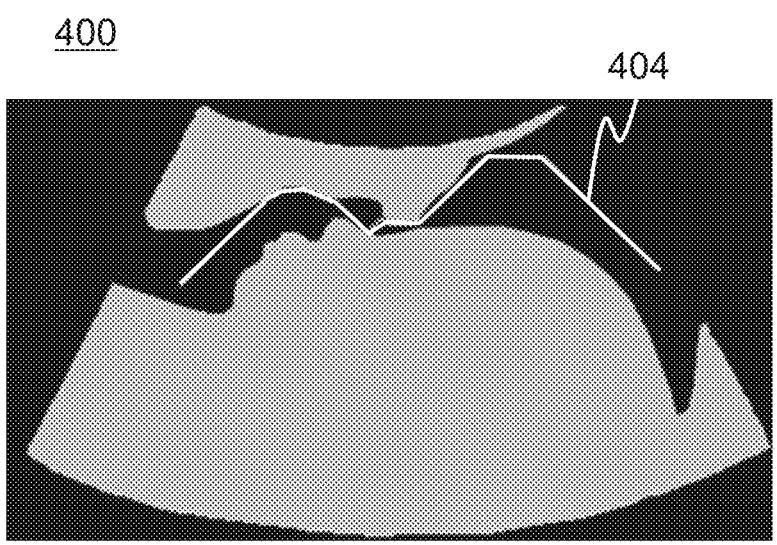
FIG. 14 illustrates one example of a corrected boundary curve of the first embodiment.

The coupler 225 couples the two curves being determined as the divided boundary curves by the validity determiner 224, respectively on the two divided images 420 and 430, and outputs the result as the boundary curve after the correction (corrected boundary curve). Thus generated corrected boundary curve 404 is displayed on the monitor 108 together with the axial image 400. FIG. 14 shows an example of the display.

[Clipping Plane Generator]

The clipping plane generator 226 generates a clipping plane from the corrected boundary curve obtained on any axial image 400. By way of example, the clipping plane generator 226 copies the corrected boundary curve on one axial image to all the other axial planes, and determines the plane containing all the corrected boundary curves, as a clipping plane.

As illustrated, the corrected boundary curve 404 obtained according to the procedure of the present embodiment is able to be established as the boundary between placenta and fetus, which is hard to be set with a spline curve. According to the clipping plane generated from this corrected boundary curve, it is possible to partition the region into a region of fetus (tissue to be imaged) and a region of an extra tissue other than the fetus (tissue not imaged), with a high degree of accuracy. Therefore, extra data other than the fetus is not used for the rendering process, and this may enhance a quality of the three-dimensional projected image finally obtained.

[Flow of Three-dimensional ROI Setting Process]

A flow of the three-dimensional ROI setting process of the present embodiment will be explained. FIG. 15 is a flow of the three-dimensional ROI setting process according to the three-dimensional ROI setter 110 of the present embodiment.

The accepting part 210 displays a tomographic image (axial image 400) on the monitor 108 (step S1101). Then, the accepting part accepts an input of a boundary curve (initial boundary curve) 401 from the user (step S1102).

The start point detector 221 detects the start point 411 from the initial boundary curve 401 (step S1103). The energy map generator 222 divides the axial image 400 by the start point 411, and generates the energy maps 421 and 431 (step S1104). The path searcher 223 searches through the energy maps 421 and 431, so as to obtain a minimum energy path (step S1105).

The validity determiner 224 determines validity of the minimum energy path being searched for, and obtains the divided boundary curves (step S1106). The coupler 225 obtains the corrected boundary curve 404 from the divided boundary curves (step S1107).

The clipping plane generator 226 generates the clipping plane on the basis of the corrected boundary curve 404 that is determined on the axial image 400, and establishes the 3D-ROI (step S1108).

As explained so far, the diagnostic image generation apparatus (ultrasound image-capturing apparatus) 100 of the present embodiment is provided with the three-dimensional ROI setter 110 configured to establish a 3D-ROI to which the rendering process is applied, on the volume data being an aggregate of data acquired from three-dimensional space within a living body, and the projected image generator 107 configured to execute the rendering process using the data within the 3D-ROI, and generate a three-dimensional projected image, the three-dimensional ROI setter 110 being provided with the accepting part 210 configured to accept an instruction from a user on a predetermined tomographic image of the volume data, and the clipping plane determiner 220 configured to determine a clipping plane that spatially separate tissue to be imaged and tissue not imaged on the 3D-ROI, and the clipping plane determiner 220 determines a boundary curve on the tomographic image, the boundary curve passing a start point that is specified by the instruction, and connecting pixels that minimize a sum of energy values obtained by reflecting a brightness value of one pixel to a brightness value of an adjacent pixel, and determines the clipping plane from the boundary curve.

The accepting part 210 accepts as the instruction, the initial boundary curve being the line intersection between a desired clipping plane and the tomographic image, and the clipping plane determiner is provided with the start point detector 221 configured to detect the start point on the initial boundary curve. The clipping plane determiner 220 is provided with the energy map generator 222 configured to divide the tomographic image into two, by the pixel line passing the start point, calculates the energy value of each pixel in each of the divided images, and generate the energy map in each of the divided images, the path searcher 223 configured to search for a minimum energy path being a path connecting pixels, the path minimizing a sum of the pixel values in each of the energy maps, a validity determiner 224 configured to determine a divided boundary curve in each of the divided images, in response to maximum distance between the initial boundary curve and the minimum energy path, and a coupler 225 configured to couple the divided boundary curves, so as to obtain a boundary curve. The validity determiner 224 may assume the initial boundary curve as the boundary curve, when the maximum distance between the initial boundary curve and the minimum energy path is equal to or larger than a predetermined distance threshold, and assume the minimum energy path as the boundary curve, when the maximum distance is smaller than the distance threshold.

In the present embodiment, the initial boundary curve 401 being set by the user is corrected to a line connecting pixels with the lowest brightness, thereby obtaining the corrected boundary curve. A line with the smallest energy is searched for by using the energy map, so as to perform the correction. Since the energy map is used for the search, the line as described above is able to be obtained from a broad view, and this may minimize error occurrence.

Therefore, according to the present embodiment, even though the curve set by the user, or the initial boundary curve 401 obtained from this curve is somewhat inaccurate, and apart of the fetus is invisible or a large portion of the placenta is included, it is possible to establish the boundary curve accurately between the placenta and the fetus, as far as only a part of the initial boundary curve 401 passes through the amniotic fluid region.

That is, a highly robust system may be achieved. This means that a higher degrees of flexibility is provided when the user performs the settings, as well as simplifying the setting works.

Further in the present embodiment, in searching for the minimum energy path, the searching direction is limited to the direction of the three pixels, and this allows calculation using a linear time. Also in searching for the minimum energy path, since there is a restriction that one point on the initial boundary curve 401 will be passed without fail, it is possible to considerably suppress the operation cost.

In addition, there is provided the validity determiner 224, and this may insure at the very least, a display using the initial boundary curve 401 that is obtained from the curve set by the user himself or herself.

As explained so far, according to the present embodiment, the curve set by the user is assumed as the base to be corrected so as to obtain an optimum curve, and it is possible to achieve quality improvement of a finally obtained three-dimensional projected image, high robust property, and enhancement of user operability. By way of example, a 3D video display of the fetus with a high quality of image and a high robust property may be obtained.

<Modification Example>

It is to be noted that the validity determining method performed by the validity determiner 224 is not limited to the method as described above. By way of example, two thresholds are established, and the validity may be determined using those thresholds. Hereinafter, a determination method in this case will be explained. In here, two thresholds being used are assumed as a first threshold th1, and a second threshold th2 that is smaller than the first threshold.

Similar to the aforementioned example, firstly, the maximum value of distance (maximum distance) 403 between the initial boundary curve 401 and the minimum energy path 402 is compared with the first threshold th1, and when the maximum distance 403 is smaller than the first threshold th1, the minimum energy path is determined as valid, and when it is equal to or larger than the first threshold th1, it is determined as invalid. In the aforementioned method, when it is determined as valid, the minimum energy path 402 is employed. In here, the distance between both is further compared with the second threshold th2, and only when the distance is equal to or smaller than th2, the minimum energy path 402 is employed, and in another case, the second threshold th2 is employed.

Figure 16A:
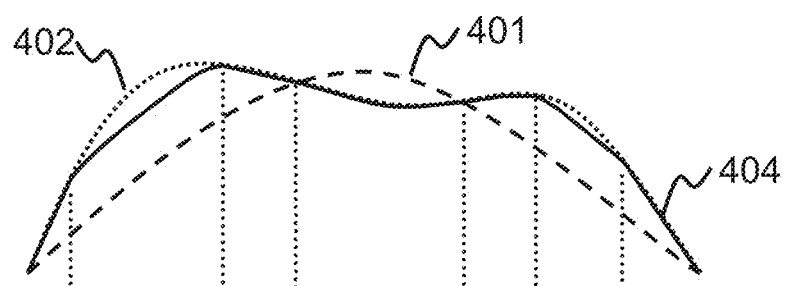
FIG. 16A and FIG. 16B illustrate the validity determination process according to a modification example of the first embodiment.
Figure 16B:
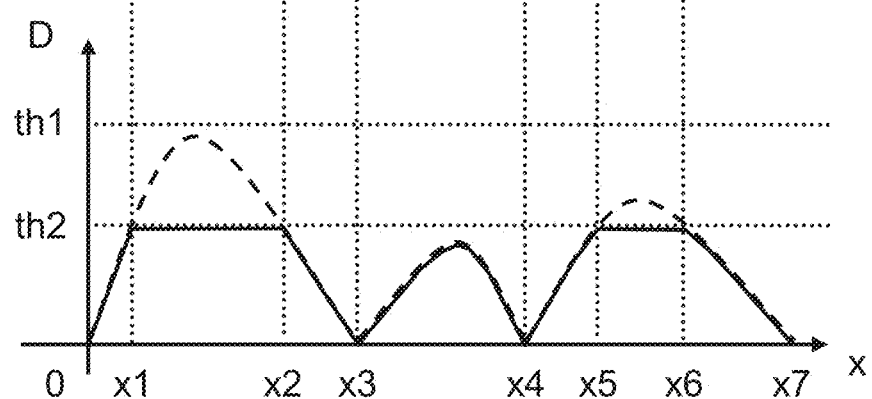

With reference to FIG. 16A and FIG. 16B, this method will be explained, with a specific example. In FIG. 16A, the broken line indicates the initial boundary curve 401, the dotted line indicates the minimum energy path 402, and the solid line indicates the boundary curve after the correction (corrected boundary curve) 404 that is finally employed. FIG. 16B illustrates the distance D between the initial boundary curve 401 and the minimum energy path 402.

In this example, the distance D between the lines is equal to or less than the second threshold th2 in the range from 0 to x1, for instance, and the minimum energy path 402 is employed. In the range from x1 to x2, since the distance D between the lines is larger than the second threshold th2, the second threshold th2 is employed. In the range from x2 to x5, since the distance D between the lines is equal to or smaller than the second threshold th2, the minimum energy path 402 is employed. In the range from x5 to x6, the distance D between the lines is larger than the second threshold th2, and thus the second threshold th2 is employed. In the range from x6 to x7 (edge part), the distance between the lines is smaller than the second threshold th2, and the minimum energy path 402 is employed.

As described above, it is possible that the validity determiner 224 determines the initial boundary curve 401 as the divided boundary curve, when the maximum distance 403 between the initial boundary curve 401 and the minimum energy path 402 is equal to or larger than the predetermined first threshold th1, determines the second distance threshold th2 as the divided boundary curve, when the maximum distance 403 is smaller than the first distance threshold th1 and equal to or larger than the second distance threshold th2 that is smaller than the first distance threshold th1, and determines the minimum energy path 402 as the divided boundary curve, when the maximum distance 403 is smaller than the second distance threshold th2.

The curves and values employed in the respective sections are connected, and a divided boundary curve is obtained. With this configuration, a curve is obtained, which utilizes the calculated minimum energy path 402 to the best effect.

<<Second Embodiment>>

Next, a second embodiment to which the present invention is applied will be explained. In the first embodiment, the user inputs the boundary curve in the same manner as a conventional example. Then, a start point for generating the energy map is determined, on the basis of the boundary curve inputted by the user, and the boundary curve is corrected assuming the start point as the point of origin. Here, in the present embodiment, the user inputs this start point, instead of the boundary curve.

The ultrasound image-capturing apparatus 100 of the present embodiment has basically the same configuration as the first embodiment. However, since the information inputted by the user is the start point, not the boundary curve, the configuration of the three-dimensional ROI setter 110a is different. Hereinafter, the present embodiment will be explained, focusing on the configuration that is different from the first embodiment.

Figure 17:
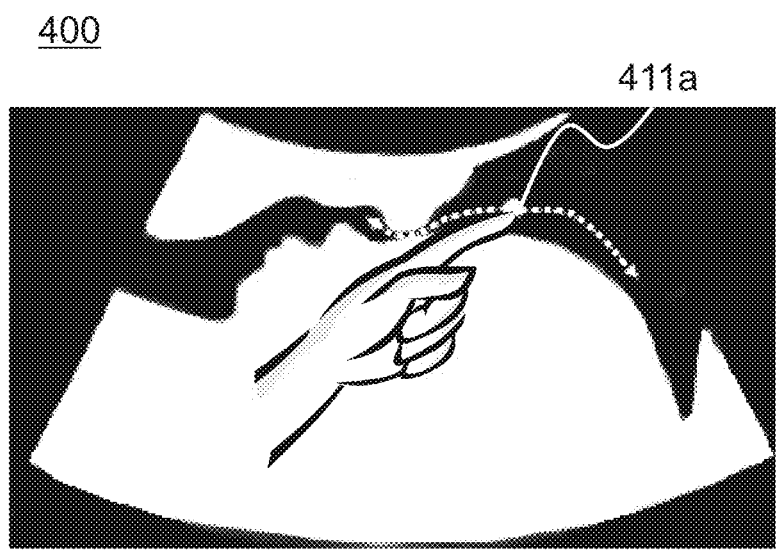
FIG. 17 illustrates setting by a user according to the second embodiment.

Also in the present embodiment, an explanation will be provided, taking as an example that a fetus is assumed as the tissue to be imaged, and the remaining tissue is assumed as the tissue not imaged. In other words, in the present embodiment as shown in FIG. 17, the user designates only one point in the amniotic fluid region between the placenta and the fetus, thereby generating the boundary curve.

Figure 18:
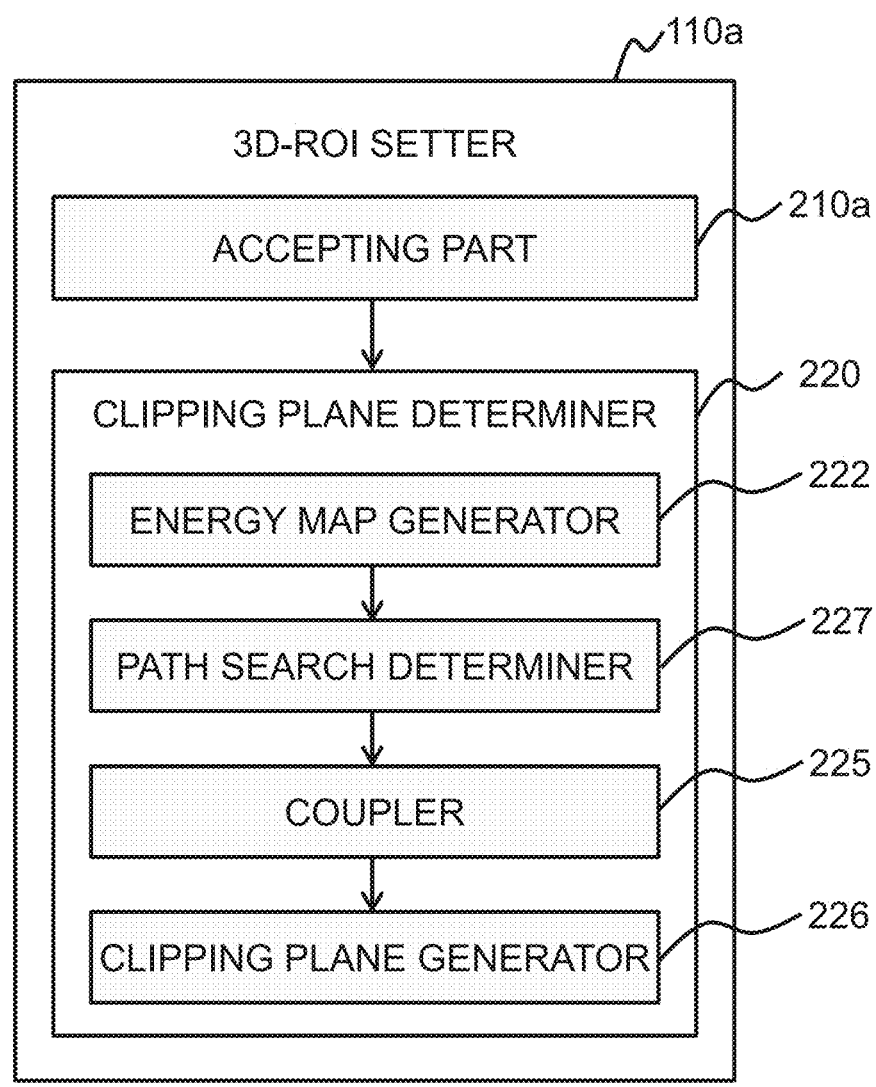
FIG. 18 is a functional block diagram showing the 3D-ROI setter of the second embodiment.

As illustrated in FIG. 18, the three-dimensional ROI setter 110a of the present embodiment is provided with the accepting part 210a configured to accept an instruction from the user, and the clipping plane determiner 220. The clipping plane determiner 220 of the present embodiment is provided with the energy map generator 222 configured to divide the tomographic image into two, by a pixel line passing the start point, calculate an energy value of each pixel in each of the divided images, and generate energy maps respectively, a path search determiner (path search determining means) 227 configured to search for a minimum energy path being a path connecting pixels that minimize a sum of the pixel values on each of the energy maps, and determine divided boundary curves respectively on the divided images, a coupler 225 configured to couple the divided boundary curves and obtain the boundary curve, and a clipping plane generator 226, and the path search determiner 227 further calculates a variance of the pixel values of at least one path candidate being obtained in searching for the minimum energy path, and assumes as the divided boundary curve, the path candidate with the sum of the pixel values being equal to or smaller than a first threshold, and the variance being equal to or smaller than a second threshold.

As described above, in the present embodiment, the information inputted by the user is assumed as the start point. Therefore, the three-dimensional ROI setter 110a of the present embodiment is not provided with the start point detector 221 as shown in FIG. 18. In addition, the processing performed in the accepting part 210a is different.

Since there is no initial boundary curve as a reference, the validity is determined simultaneously with searching for a minimum energy path. Therefore, the path search determiner 227 is provided instead of the path searcher 223 and the validity determiner 224.

[Accepting Part]

As shown in FIG. 17, the accepting part 210a of the present embodiment displays a predetermined tomographic image on the monitor 108, out of the tomographic images generated by the image processor 105, and accepts on the image, a designation of the start point 411a from the user. In the present embodiment, an explanation will be provided, taking as an example that the axial image 400 is displayed as the tomographic image.

The monitor 108 is provided with a touch panel, similar to the first embodiment, and accepts a designation of the start point 411a from the user. The user designates and inputs one point in the amniotic fluid region between the placenta and the fetus.

[Energy Map Generator]

The processing of the energy map generator 222 of the present embodiment is basically the same as the first embodiment. In other words, according to the start point 411a set by the user, the axial image 400 is divided into two, and the energy maps 421 and 431 are generated respectively in the two images 420 and 430.

[Path Search Determiner]

The path search determiner 227 is a processor serving as both the path searcher 223 and the validity determiner 224 of the first embodiment. In other words, in each of the divided images 420 and 430, the path search determiner 227 searches for a path tracking the minimum energy values of the energy maps 421 and 431, so as to generate the minimum energy path 402, and also determines the validity. Since the initial boundary curve does not exist as a criterion in the present embodiment, the following method is employed for the determination.

The path search determiner 227 starts searching from the pixels (search start points) 422 and 432 at the ends of the energy map, according to a method similar to the first embodiment. In the present embodiment, not only the energy additional value but also a variance is calculated, with respect to each path candidate i.

Specifically, the following formula (3) and formula (4) are calculated, as to each path candidate i.

$$\overline{EM} = \frac{1}{m}\sum_{i=1}^{m} EM(R_i) \qquad (3)$$

$$EM\sigma^2 = \frac{1}{m}\sum_{i=1}^{m} (EM(R_i) - \overline{EM})^2 \qquad (4)$$

Then, in addition to the total energy value of each path candidate i, judgment using each path variance $EM\sigma^2$ is provided. In other words, a path to be selected has the total energy value being equal to or smaller than the first threshold T1, and the variance $EM\sigma^2$ being equal to or smaller than the second threshold T2. Then, the path being selected is outputted as the divided boundary curve after the correction.

In this case, if there is no path meeting the aforementioned conditions, it is presented to the user that the region of interest (ROI) is not settable, prompting the user to add another designated point in the amniotic fluid region.

[Coupler and Clipping Plane Generator]

The coupler 225 of the present embodiment couples the divided boundary curves after the correction, being calculated in the two divided images 420 and 430, similar to the first embodiment, generates the corrected boundary curve 404, and displays the corrected boundary curve 404 on the axial image 400. In addition, the clipping plane generator 226 further generates a clipping plane from the corrected boundary curve 404, similar to the method of the first embodiment.

[Flow of Three-Dimensional ROI Setting Process]

Figure 19:
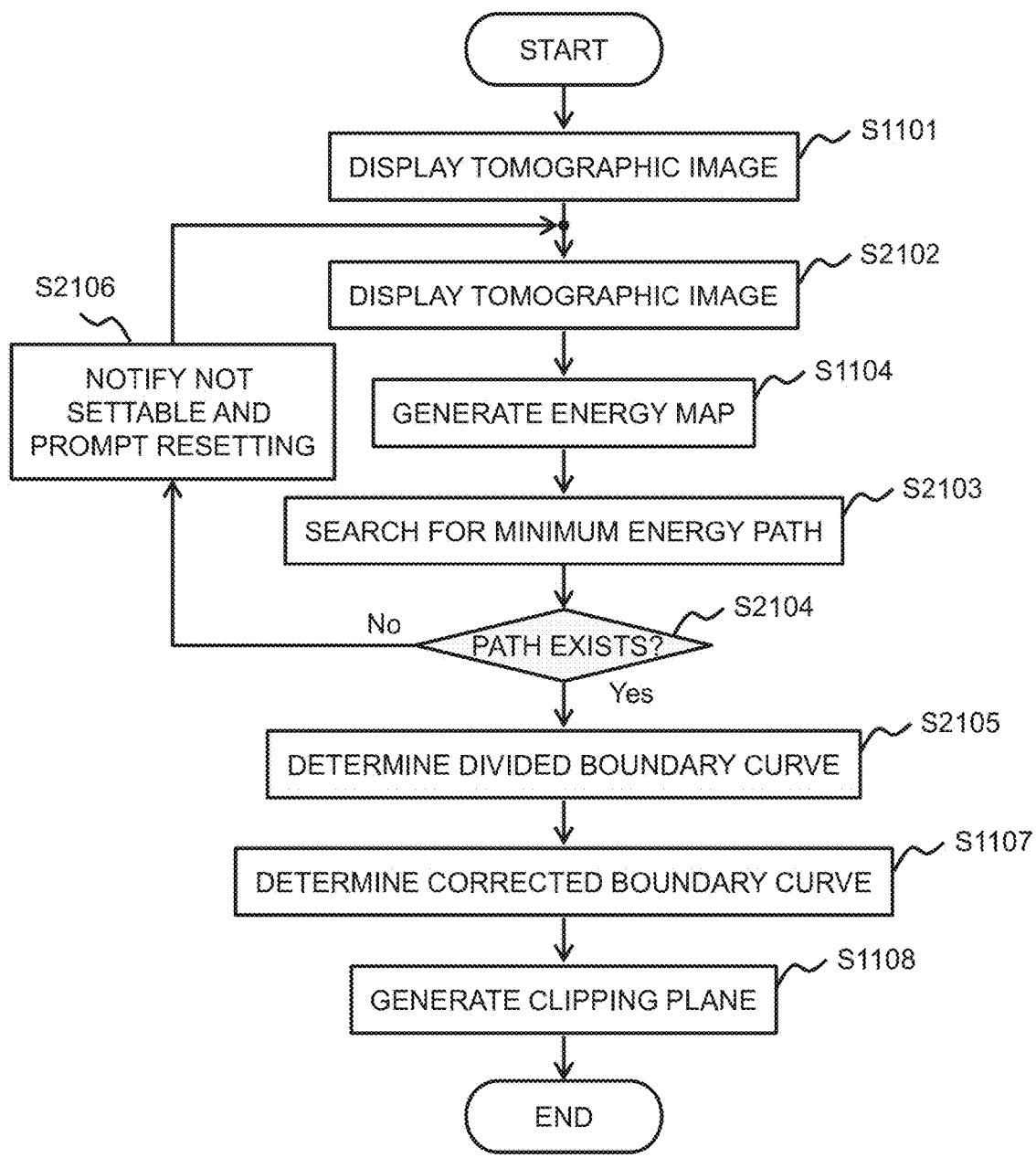
FIG. 19 is a flowchart showing the 3D-ROI setting process of the second embodiment.

Next, an explanation will be provided as to a flow of the three-dimensional ROI setting process according to the three-dimensional ROI setter 110a of the present embodiment. FIG. 19 is a flow of the three-dimensional ROI setting process of the present embodiment.

The accepting part 210a displays the tomographic image (axial image 400) on the monitor 108 (step S1101). Then, the accepting part accepts an input of the start point 411a from the user (step S2102). The energy map generator 222 divides the axial image 400 by the start point 411a, and generates the energy maps 421 and 431, respectively in the divided images 420 and 430 (step S1104).

The path search determiner 227 starts searching for a minimum energy path, according a method similar to the first embodiment (step S2103). In the present embodiment, as to each path candidate i, not only the energy additional value, but also a variance is calculated.

The path search determiner 227 determines whether or not there exists the minimum energy path that meets the aforementioned conditions (step S2104).

If there exists a path that satisfies the aforementioned conditions, the path search determiner 227 outputs the minimum energy path as the divided boundary curve (step S2105). Then, the coupler 225 obtains a corrected boundary curve 404 from the divided boundary curves (step S1107).

The clipping plane generator 226 generates a clipping plane on the basis of the corrected boundary curve 404 determined on the axial image 400, and establishes the 3D-ROI (step S1108).

If there is no path that meets the aforementioned conditions, the path search determiner 227 presents the user that the region of interest (ROI) is not settable, and prompts the user to add another start point in the amniotic fluid region (step S2106).

Upon accepting the designation of a new start point 411a, the process returns to the step S2102.

As explained so far, the diagnostic image generation apparatus (ultrasound image-capturing apparatus) 100 of the present embodiment is provided with the three-dimensional ROI setter 110a and the projected image generator 107, similar to the first embodiment. Then, the three-dimensional ROI setter 110a of the present embodiment is provided with the accepting part 210a configured to accept an instruction from the user, on a predetermined tomographic image of the volume data, and the clipping plane determiner 220 determines a boundary curve on the tomographic image, a boundary curve passing a start point that is specified by the instruction, and connecting pixels that minimize a sum of energy values obtained by reflecting a brightness value of one pixel to a brightness value of an adjacent pixel, and determines the clipping plane from the boundary curve.

The accepting part 210a accepts the start point as the instruction, the clipping plane determiner 220 is provided with the energy map generator 222 configured to divide the tomographic image into two by a pixel line passing the start point, calculate an energy value of each pixel in each of the divided images, and generate energy maps respectively, the path search determiner 227 configured to search for a minimum energy path connecting pixels that minimize a sum of the pixel values on each of the energy maps, and determine divided boundary curves respectively on the divided images, and the coupler 225 configured to couple the divided boundary curves so as to obtain the boundary curve, and the path search determiner 227 further calculates a variance of the pixel values in each of at least one path candidate that is obtained in searching for the minimum energy path, and assumes as the divided boundary curve, a path candidate with a sum of the pixel values being equal to or smaller than the first threshold, and the variance being equal to or smaller than the second threshold.

According to the present embodiment, the energy map is used to assume a line with the minimum energy as the corrected boundary curve, on the basis of the start point designated by the user. Accordingly, it is possible to obtain an effect similar to the effect of the first embodiment.

As described so far, in the present embodiment, just one point is designated by the user in the amniotic fluid region between the placenta and the fetus to generate the boundary curve, allowing the 3D-ROI to be established. Therefore, this may enhance user's operability drastically. In other words, the user is only required to designate just one point, and this may achieve a high quality fetal three-dimensional projected image, for instance, according to a simple operation.

When it is determined that the reliability of the generated curve is low, according to determination of the validity, the user is notified of the situation, prompting the user to change the designated point. This may further improve the precision in setting the 3D-ROI, and consequently, the accuracy of the finally obtained three-dimensional projected image may be enhanced.

In the present embodiment, the judgment is made using the energy value as a reliability index, basically. This process of searching for and determining the minimum energy path of the present embodiment is also applicable to the first embodiment.

On the other hand, it is further possible to configure such as generating a curve model in advance, and assuming this curve model as the initial boundary curve of the first embodiment. Then, according to a method similar to the first embodiment, the minimum energy path searching process and the validity determination process may be performed. The curve model may be generated by accumulating data of the curves (fetal shape) between the placenta and the fetus, for instance, and extracting a feature amount of the data by the use of machine learning.

<Modification Example>

Figure 20:
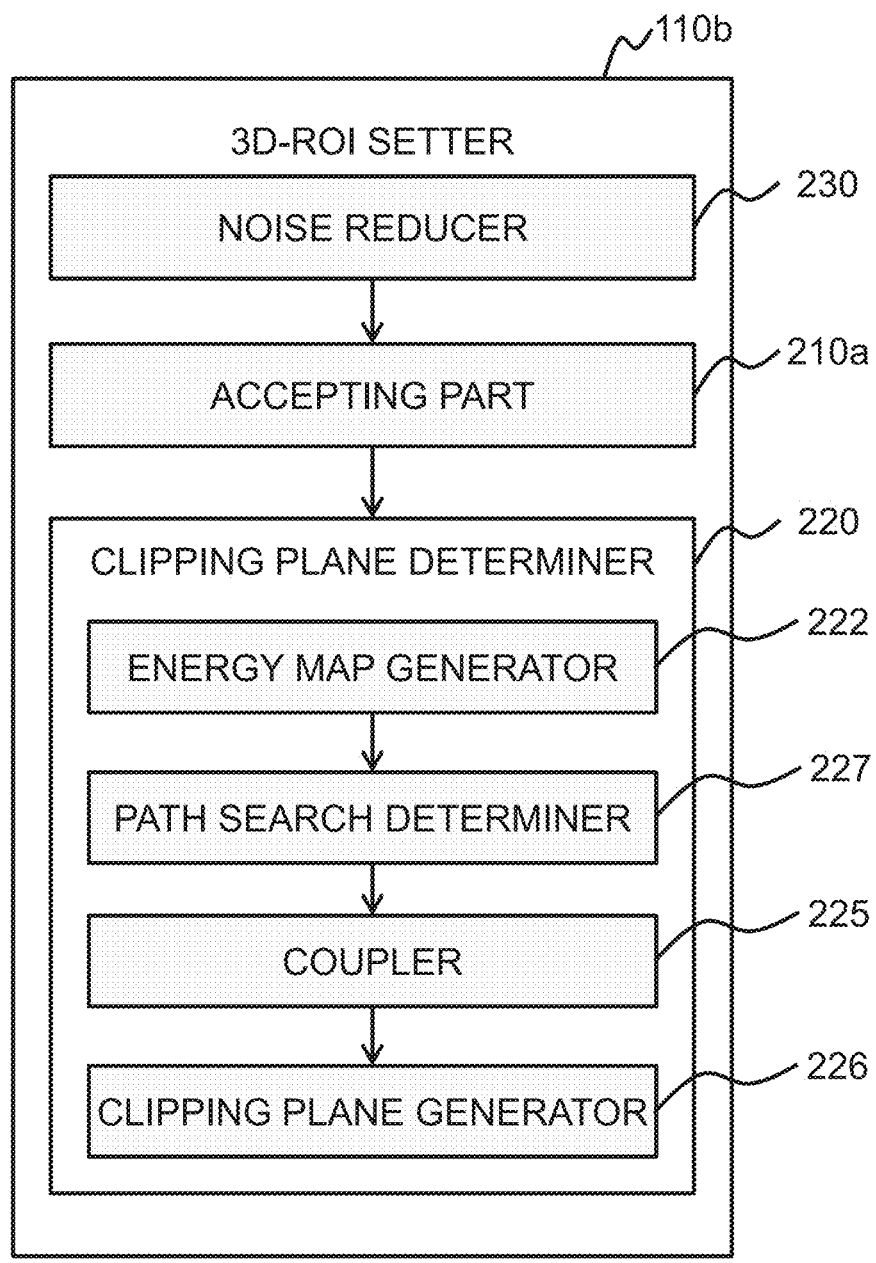
FIG. 20 is a functional block diagram showing the 3D-ROI setter according to the modification example of the second embodiment.

As shown in FIG. 20, the three-dimensional ROI setter 110b may further be provided with a noise reducer 230 configured to perform noise reduction process.

The noise reducer 230 applies the noise reduction process to the tomographic image (here, the axial image 400) that is used in the process performed by the three-dimensional ROI setter 110b. The noise reduction process may include a smoothing process and a filtering process, such as Gaussian smoothing and Median filtering. It is desirable that a filter used in the filtering process is an edge preserving type, such as bilateral filter and Guided Filter, which removes only the noise caused by a floating substance, multiple reflection, and the like, within the amniotic fluid having a relatively low brightness value, and holds the shape information of the fetus.

The accepting part 210a presents the user the axial image 400 after the noise is reduced and then accepts the designation of the start point 411. The energy map generator 222 uses the axial image 400 after the noise is reduced and generates the energy maps 421 and 431.

According to this procedure, the smoothing process is performed sufficiently and the energy maps are generated on the image showing only a schematic shape after removing the floating substances, and the like. Therefore, this may enhance the accuracy of the energy maps 421 and 431 being generated, further improving the accuracy of the finally obtained boundary curve, and the accuracy of the 3D-ROI.

It is to be noted that the coordinate converter 106 and the projected image generator 107 use the tomographic image before the noise reduction process, not the smoothed image, and generate the volume data and the three-dimensional projected image.

In addition, the noise reduction process applied to the tomographic image used by the three-dimensional ROI setter 110b is also applicable in the first embodiment in the same manner.

<<Third Embodiment>>

The third embodiment of the present invention will be explained. In the present embodiment, the corrected boundary curve generated by the three-dimensional ROI setter of the first embodiment or the second embodiment is further correctable by the user. Hereinafter, the present embodiment will be explained taking as an example the case where this function is added to the second embodiment.

It is assumed that the configuration of the ultrasound image-capturing apparatus 100 of the present embodiment is basically the same as the second embodiment. As shown in FIG. 21, the three-dimensional ROI setter 110c of the present embodiment is also provided with basically the same configuration as the second embodiment.

As illustrated, the three-dimensional ROI setter 110c of the present embodiment is provided with the accepting part 210a configured to accept an instruction from the user on a predetermined tomographic image of volume data, and the clipping plane determiner 220 configured to determine a clipping plane that spatially separates tissue to be imaged and tissue not imaged in the 3D-ROI. The clipping plane determiner 220 of the present embodiment is provided with the energy map generator 222, the path search determiner 227, the coupler 225, and the clipping plane generator 226, similar to the second embodiment. The clipping plane determiner 220 of the present embodiment is further provided with a corrector (correcting means) 228 configured to correct the boundary curve, and the corrector 228 accepts an additional designated point on the boundary curve, and corrects the boundary curve to a curve that passes the additionally designated point, and connects pixels with a minimum brightness value.

The corrector 228 accepts an instruction of correction from the user, so as to further correct the divided boundary curve after the correction that is generated by the path search determiner 227. The corrector 228 of the present embodiment displays the calculated boundary curve on the selected tomographic image (axial image 400), and accepts the instruction of correction via this display. In other words, the corrector 228 corrects the curve according to an additional instruction from the user.

Figure 22A:
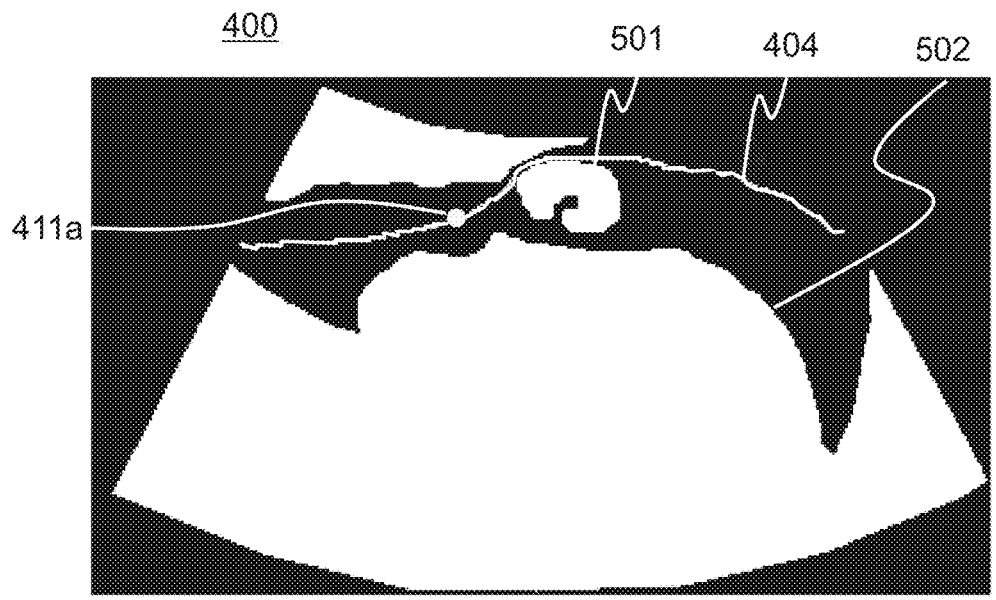
FIG. 22A and FIG. 22B illustrate a correction process of the third embodiment.
Figure 22B:
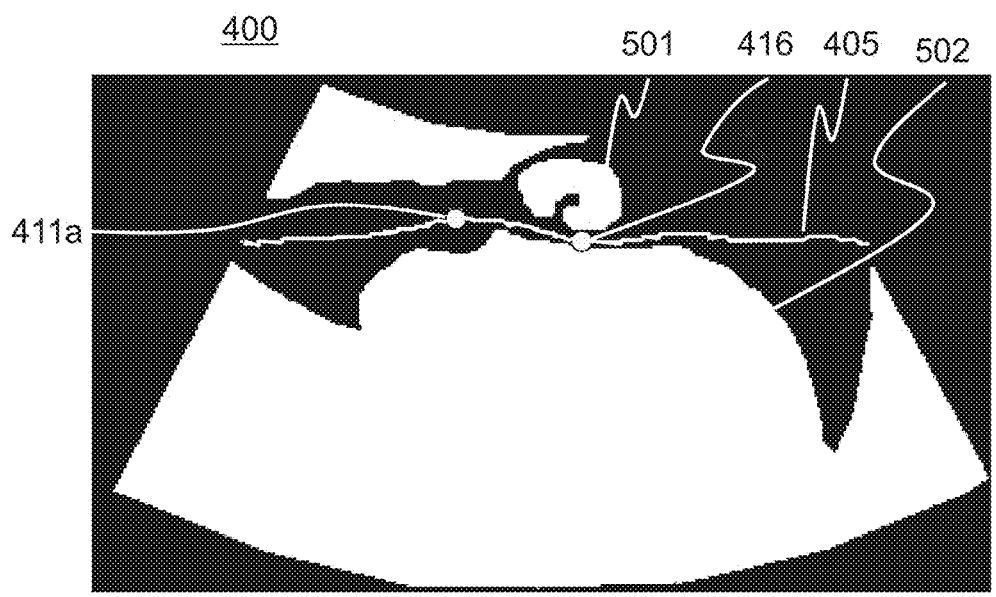

FIG. 22A illustrates the corrected boundary curve 404 that is generated according to the designation of the start point 411a by the user. Using this display, the corrector 228 of the present embodiment accepts an instruction to additionally designate the point 416, as shown in FIG. 22B. Then, upon receipt of this instruction, the corrector 228 corrects the corrected boundary curve 404, to the curve 405 that passes both the start point 411a and the point additionally designated (additional designated point) 416.

In FIG. 22A and FIG. 22B, the reference numeral 501 indicates the arm of the fetus. The corrected boundary curve 404 initially generated passes above the fetal arm 501. Therefore, if the clipping plane is generated on the basis of the boundary curve 404, the 3D-ROI includes the fetal arm 501. The user's designation of the additional point 416 may allow the arm 501 to be excluded from the 3D-ROI, and only a portion of the face 502 to be established as the imaging target region.

Upon accepting the additional designated point 416, the corrector 228 assumes this additional designated point 416 as the start point, and activates each part (the energy map generator 222, the path search determiner 227, and the coupler 225) in the same manner as the second embodiment, so as to generate a corrected boundary curve passing the additional designated point 416. In this case, the corrector generates the corrected boundary curve in such a manner as passing the previously designated start point 411a as well.

Figure 23:
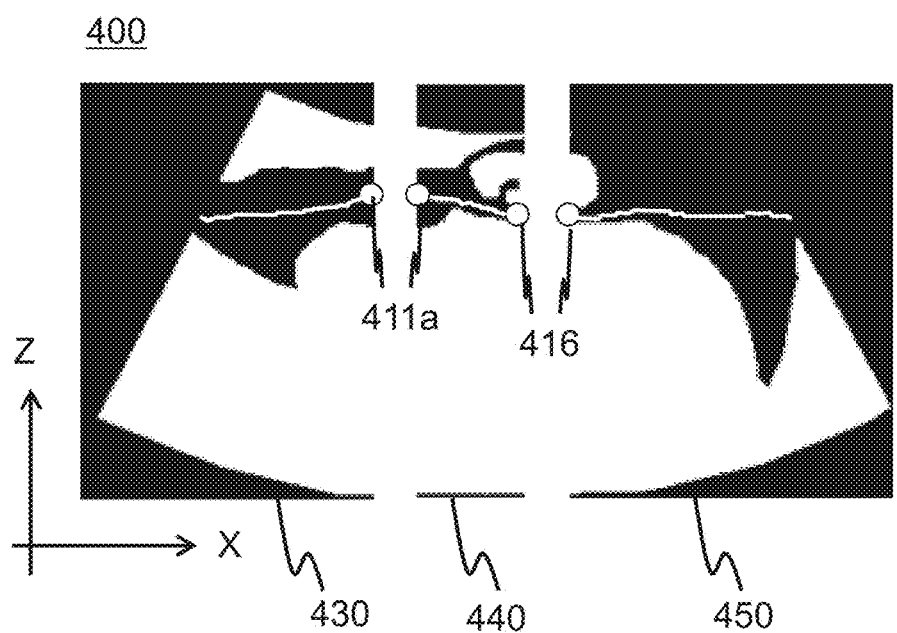
FIG. 23 illustrates the correction process of the third embodiment.

As shown in FIG. 23, the corrector 228 assumes the start point 411a and the additional designated point 416 as points of origin, and divides the image into three (divided images 430, 440, and 450). In the divided images 440 and 450, searching for the minimum energy path and determining the validity as explained in the second embodiment are performed.

Specifically, as shown in FIG. 23, the line passing the start point 411a in the z-axis direction, and the line passing the additional designated point 416 in the z-axis direction divide the axial image 400. Then, in the region between the start point 411a and the additional designated point 416 (the divided image 440), and in the region between the additional designated point 416 and the end on the opposite side of the start point 411a (the divided image 450), the divided boundary curves after the correction are generated assuming the additional designated point 416 as the start point, according to the method similar to the second embodiment.

In this case, there is a constraint condition that in the divided image 440, the curve passes both the start point 411a and the additional designated point 416. In other words, in the divided image 440, a path passing the additional designated point 416 and having the minimum energy is selected, from the path candidates passing the start point 411a.

The coupler 225 connects thus generated divided boundary curves, to be outputted as the corrected boundary curve 405, and then it is displayed on the axial image 400 as shown in FIG. 22B.

In the present embodiment, in the process of searching for and determining the minimum energy path according to the path search determiner 227, it is alternatively possible to employ a method that intentionally sets a minimum value as the energy value of the additional designated point 416, and retries the search so that the path passes the additional designated point 416 without fail.

The number of times for setting the additional designated point 416 by the user is not particularly limited. Every time the additional designated point 416 is provided, the corrector 228 divides the tomographic image (axial image 400) according to the aforementioned method and updates the corrected boundary curve.

The number of the additional designated point 416 being accepted at one time is not limited to one point. It is possible to configure as accepting from the user, an input of plural additional designated points 416. The corrector 228 divides the axial image 400 by the lines respectively passing the additional designated points 416, and the process of searching for and determining the minimum energy path is performed in each of the divided images, so as to determine the divided boundary curve. In this case, there is a constraint condition that the lines have to pass the additional designated points 416 on both ends, respectively.

In this case, the corrector 228 may activate the energy map generator 222 and the path search determiner 227 in parallel in association with the number of the additional designated points 416 provided by the user, that is, the division number of the axial image 400.

As explained so far, the diagnostic image generation apparatus (ultrasound image-capturing apparatus) 100 of the present embodiment is provided with the three-dimensional ROI setter 110c and the projected image generator 107, similar to the second embodiment. Then, the three-dimensional ROI setter 110c of the present embodiment is further provided with the corrector 228 configured to correct the boundary curve, and the corrector 228 accepts an additional designated point on the boundary curve, and corrects the boundary curve to obtain a curve that passes the designated point and connects the pixels with the minimum brightness value.

As described above, in the present embodiment, the boundary curve being generated is presented to the user, in such a manner as superimposed on the tomographic image, and if there is an additional instruction from the user, further correction is applied. According to the present embodiment, the user is allowed to correct the generated boundary curve, according to his or her taste, a type of diagnosis, and the like. In addition, inputting of plural designated points enables more quick acquisition and display of a three-dimensional projected image required by the user.

According to the present embodiment, it is possible to achieve displaying of a three-dimensional projected image of a fetus, for instance, with a simple operation and a high degree of accuracy.

In the present embodiment, the start point 411a and the additional designated point 416 may be changeable. In other words, it may be configured such that when the tomographic image 400 is displayed, the start point 411a and the additional designated point 416 are displayed together with the boundary curve, and accepts an instruction to cancel either of the start point 411a and the additional designated point 416 being currently set. Then, recalculation is performed to obtain the boundary curve that passes only the remaining start point 411a or the remaining additional designated point 416. This process indicates, for example, to resume the boundary curve 404 of FIG. 22A from the boundary curve 405 of FIG. 22B.

The present embodiment has been explained, taking as an example that the original corrected boundary curve 404 is generated according to the method of the second embodiment, but it is alternatively possible to obtain the original corrected boundary curve 404 according to the method of the first embodiment.

<<Fourth Embodiment>>

Next, the fourth embodiment of the present invention will be explained. In the present embodiment, the boundary curve may be corrected also on plural second tomographic planes being orthogonal to the first tomographic plane, in the similar manner as the case of the first tomographic plane. Hereinafter, an explanation will be provided, taking as an example the case where an axial plane is assumed as the first tomographic plane, and a sagittal plane is assumed as the second tomographic plane.

Figure 24:
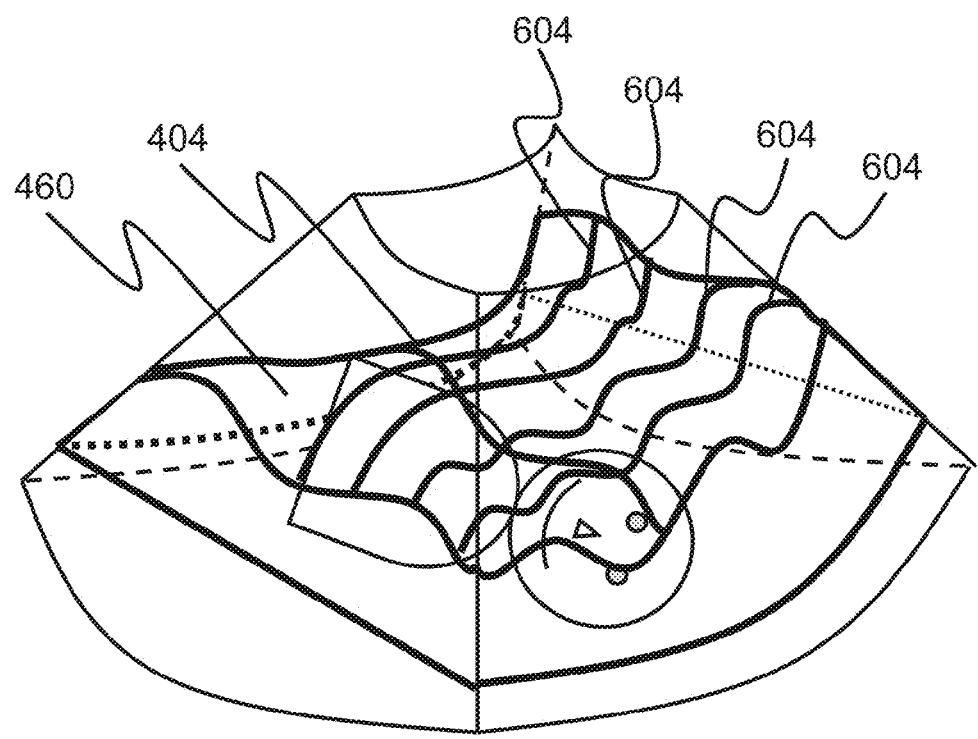
FIG. 24 illustrates a clipping plane generation process of the fourth embodiment.

As illustrated in FIG. 24, in the present embodiment, firstly by using the axial plane, the corrected boundary curve 404 is determined, according to the method of the second embodiment. Next, in each of the predetermined plural sagittal planes, the corrected boundary curve 604 is generated. In this case, an intersection point between the corrected boundary curve 404 and each of the sagittal plane is assumed as the start point. Then, in each of the sagittal plane, the corrected boundary curve 604 is generated according to the method of the second embodiment. Then, the plane including the corrected boundary curves 404 and corrected boundary curves 604 entirely is generated as the clipping plane 460.

Figure 25:
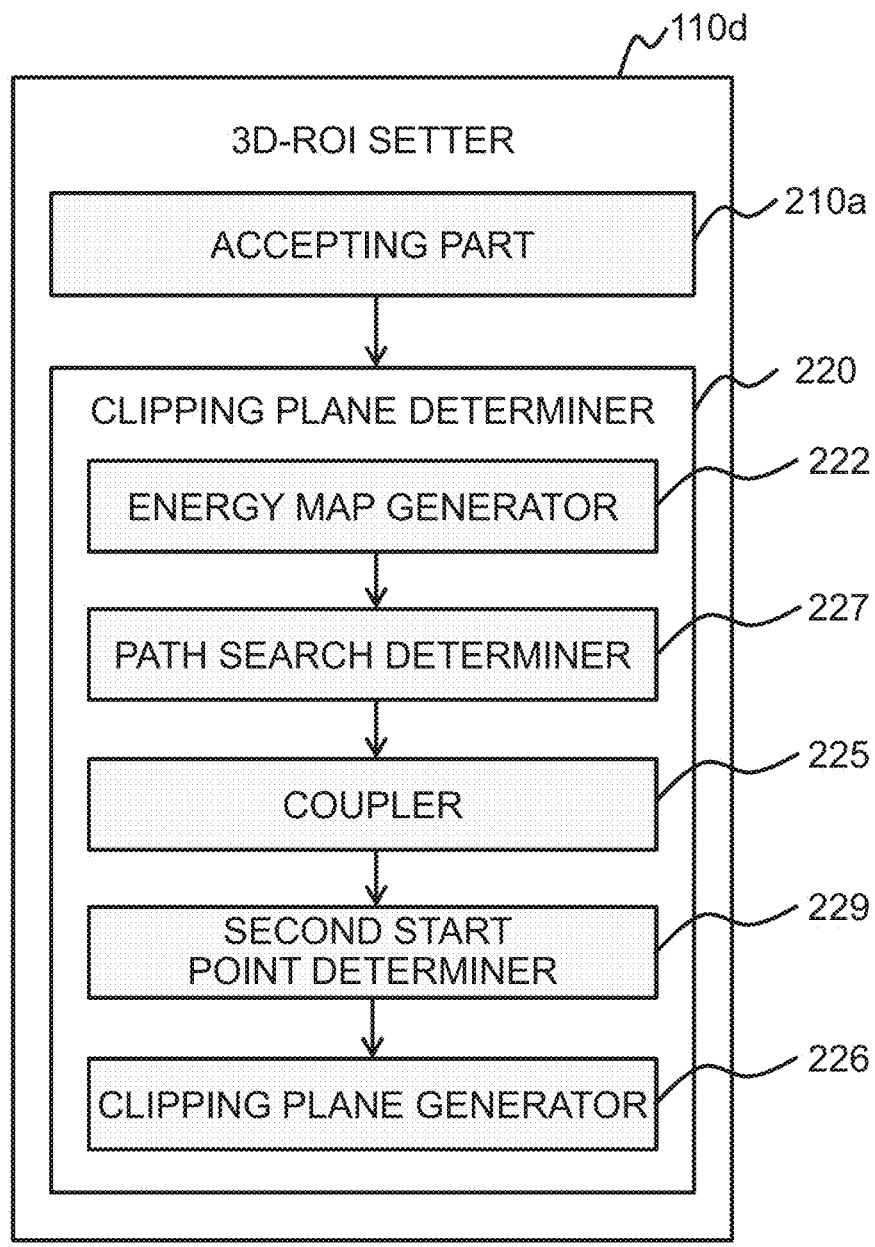
FIG. 25 is a functional block diagram showing the 3D-ROI setter of the fourth embodiment.

The ultrasound image-capturing apparatus 100 of the present embodiment basically has the same configuration as the second embodiment. The three-dimensional ROI setter 110d of the present embodiment also has basically the same configuration as the second embodiment. However, in the present embodiment, the corrected boundary curve 404 on the axial plane is used to set the start point on the plural sagittal planes. Therefore, as shown in FIG. 25, the three-dimensional ROI setter 110d of the present embodiment is further provided with the second start point detector (second start point detecting means) 229. The process performed by the clipping plane generator 226 is also different.

[Second Start Point Detector]

The second start point detector 229 of the present embodiment detects an intersection point of the corrected boundary curve 404 generated by the coupler 225, and at least one predetermined sagittal plane, and assumes the intersection point as the start point of each sagittal plane. One or more sagittal planes are determined in advance.

[Clipping Plane Generator]

When the corrected boundary curve 604 is generated on each sagittal plane, the clipping plane determiner 220 of the present embodiment connects the corrected boundary curves 404 generated on the axial plane in advance, with the plural corrected boundary curves 604, thereby generating the clipping plane. In other words, the clipping plane determiner 220 of the present embodiment further determines on a tomographic image that is orthogonal to the aforementioned tomographic image, a second boundary curve that passes the start point being the intersection point with the boundary curve, and connects the pixels with the minimum brightness value, and generates as the clipping plane, a plane including the boundary curves and the second boundary curves.

Specifically, as shown in FIG. 24, as for the axial plane, the boundary curve 404 generated on the predetermined axial plane is copied, as it is, to all the other axial planes.

As for the sagittal plane, expansion is performed by using the boundary curves 604 generated on the aforementioned plural sagittal planes. With regard to the sagittal plane for which the sagittal plane boundary curve 604 is not generated, the boundary curve 604 of the sagittal plane generated by the adjacent boundary curve is copied as it is, or weights are assigned according to the distance between the sagittal planes so as to perform interpolation, thereby generating the boundary curve.

Those plural sagittal planes are established in advance. It is to be noted that the distance between the sagittal planes may be equal, or unequal but constant. The distance may be user-definable or it may be predetermined.

[Three-Dimensional ROI Setting Process]

Figure 26:
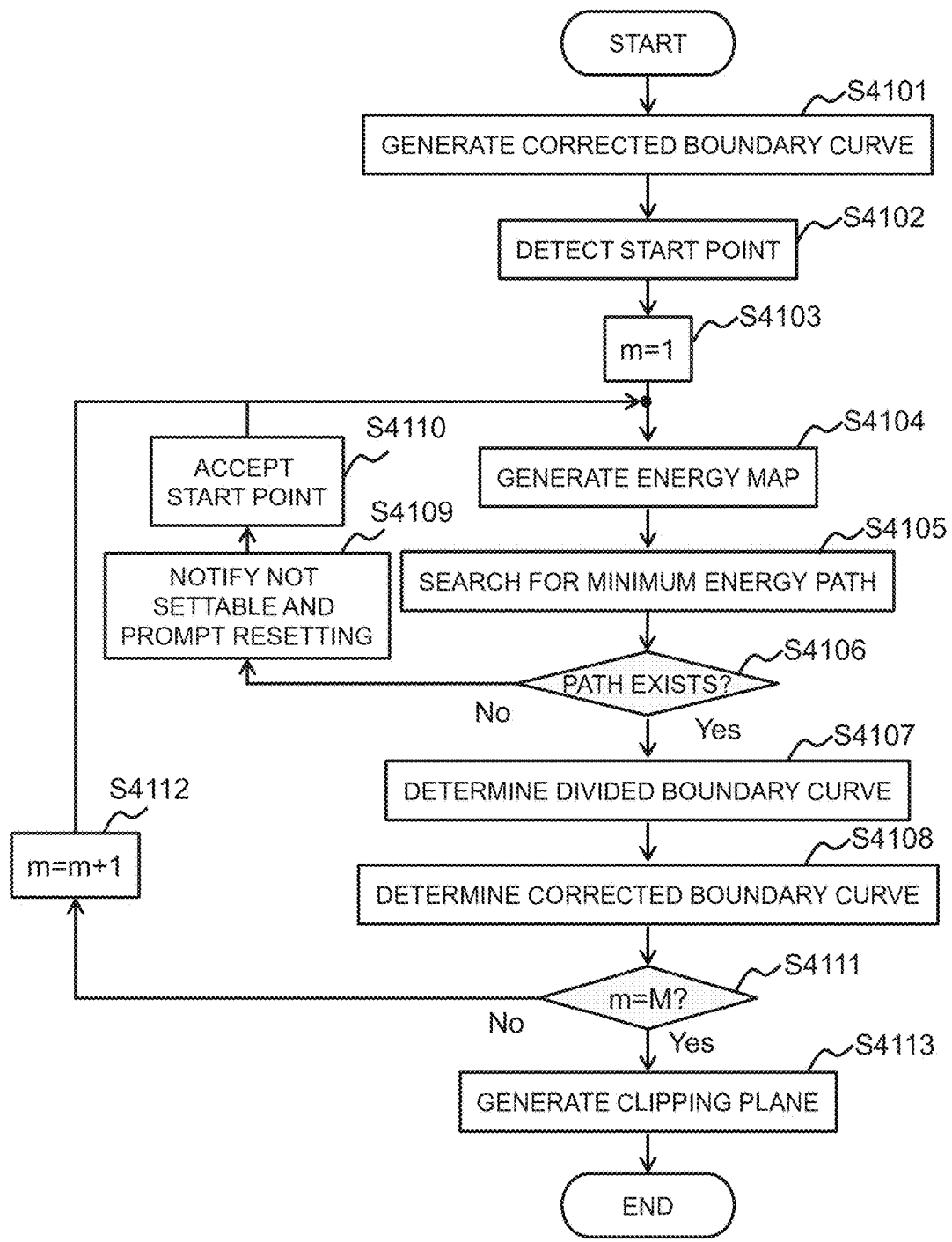
FIG. 26 is a flowchart showing the 3D-ROI setting process of the fourth embodiment.

FIG. 26 is a flow of the three-dimensional ROI setting process of the present embodiment. In here, M (M is an integer at least one) sagittal plane is used to generate the corrected boundary curve 604.

Each part of the three-dimensional ROI setter 110d executes the three-dimensional ROI setting process from S1101 to S1107 of the second embodiment, and generates the corrected boundary curve 404 on the axial image 400 (step S4101).

The second start point detector 229 detects the intersection point between each sagittal plane and the corrected boundary curve 404, thereby obtaining the start point of each sagittal plane (step S4102).

Following processing from the step S4104 to step S4108 is performed as to each of the sagittal planes (steps S4103, S4111, and S4112).

The energy map generator 222 generates an energy map from the start point being detected (step S4104). The path search determiner 227 searches for the minimum energy path (step S4105), and determines whether or not there is any minimum energy path that meets the conditions that are explained in the second embodiment (step S4106). If there is a path that meets the conditions, the path search determiner 227 outputs this path as the divided boundary curve (step S4107). Then, the coupler 225 obtains the corrected boundary curve 604 from the divided boundary curves (step S4108).

On the other hand, in the step S4106, if there is no path that meets the conditions, the user is notified that the path is not settable, together with prompting the user to establish a new start point (step S4109). When the accepting part 210a accepts the start point (step S4110), the process shifts to the step S4104, and continues the processing.

Finally, the clipping plane generator 226 generates the clipping plane from the corrected boundary curves 404 generated in the step S4101, and the corrected boundary curves 604 generated in the step S4108 (step S4113).

As explained so far, the diagnostic image generation apparatus (ultrasound image-capturing apparatus) 100 of the present embodiment is provided with the three-dimensional ROI setter 110d and the projected image generator 107, similar to the first embodiment. Similar to the second embodiment, the three-dimensional ROI setter 110d of the present embodiment is provided with the accepting part 210a configured to accept an instruction from the user on the predetermined tomographic image of the volume data, and the clipping plane determiner 220 configured to determine in the 3D-ROI, the clipping plane that spatially separates the tissue to be imaged and the tissue not imaged, and the clipping plane determiner 220 further determines the second boundary curve that passes the start point being the intersection point of the boundary curve on the second tomographic image being orthogonal to the aforementioned tomographic image, and connects the pixels with the minimum brightness value, and the clipping plane generator 226 generates as the clipping plane, the surface including the boundary curves and the second boundary curves.

As described above, according to the present embodiment, the boundary curve is corrected to a line connecting the pixels with the lowest brightness value, according to the setting by the user, so as to determine the clipping plane from the boundary curves after the correction. Therefore, similar to each of the aforementioned embodiments, it is possible to obtain the boundary curve between the region to be imaged and the region not imaged, with a high degree of accuracy. Consequently, a highly accurate three-dimensional projected image may be obtained.

According to the present embodiment, the same processing is applied to the sagittal plane, in generating the 3D-ROI. Therefore, the boundary curve between the region to be imaged and the region not imaged is determined multidirectionally. Eventually, it is possible to establish the 3D-ROI with a high degree of accuracy and generate highly precise volume data, from which floating substances and noise other than the region of interest (ROI) have been removed.

It is to be noted that in the present embodiment, the corrected boundary curve 404 may be generated according to the first embodiment or the third embodiment.

What is claimed is:

1. A diagnostic image generation apparatus, comprising:
a processor; and
a memory coupled to the processor and which stores instructions that cause the processor to execute:
a three-dimensional region of interest (ROI) setter configured to establish a three-dimensional ROI on volume data being an aggregate of data acquired from three-dimensional space within a living body, and
a projected image generator configured to execute a rendering process on the data within the three-dimensional ROI, and generate a three-dimensional projected image,
wherein the three-dimensional ROI setter includes:
an accepting part configured to accept an instruction from a user on a predetermined tomographic image of the volume data and an initial boundary curve being a line intersection of a desired clipping plane and the tomographic image, and
a clipping plane determiner configured to determine a clipping plane that spatially separates tissue to be imaged and tissue not to be imaged in the three-dimensional ROI,
wherein the clipping plane determiner determines a first boundary curve on the tomographic image, the first boundary curve passing a start point and being a path connecting pixels that minimizes a sum of energy values calculated from respective pixel values of the pixels, and determines the clipping plane from the first boundary curve,
wherein the clipping plane determiner includes:
a start point detector configured to detect the start point on the initial boundary curve,
an energy map generator configured to divide the tomographic image into two, by a line of the pixels passing the start point, calculate the energy values of each of the pixels in each of the images being divided, and generate respective energy maps therefrom,
a path searcher configured to search for a minimum energy path being a path connecting the pixels that minimizes the sum of the energy values in each of the energy maps,
a validity determiner configured to determine a divided boundary curve in each of the divided images in response to a maximum distance between the initial boundary curve and the minimum energy path, and
a coupler configured to couple the divided boundary curves so as to obtain the first boundary curve.

2. The diagnostic image generation apparatus according to claim 1, wherein the clipping plane determiner further includes:
a corrector configured to accept a designated point provided on the first boundary curve, and correct the first boundary curve to pass the designated point and connect the pixels with a minimum brightness value.

3. The diagnostic image generation apparatus according to claim 1, wherein the clipping plane determiner is further configured to:
determine a second boundary curve that passes the start point being an intersection point of the first boundary curve on another tomographic image being orthogonal to the tomographic image, connect the pixels with a minimum brightness value, and determine the clipping plane which includes the first boundary curve and the second boundary curve.

4. The diagnostic image generation apparatus according to claim 1, wherein the validity determiner is further configured to:

assume the initial boundary curve as the first boundary curve, when the maximum distance between the initial boundary curve and the minimum energy path is equal to or larger than a predetermined distance threshold, and assume the minimum energy path as the first boundary curve, when the maximum distance is smaller than the predetermined distance threshold.

5. The diagnostic image generation apparatus according to claim 1, wherein the validity determiner is further configured to:

assume the initial boundary curve as the first boundary curve, when the maximum distance between the initial boundary curve and the minimum energy path is equal to or larger than a first distance threshold, assume a second distance threshold as the first boundary curve, when the maximum distance is smaller than the first distance threshold and equal to or larger than a second distance threshold that is smaller than the first distance threshold, and assume the minimum energy path as the first boundary curve when the maximum distance is smaller than the second distance threshold.

6. A diagnostic image generation apparatus, comprising:
a processor; and
a memory coupled to the processor and which stores instructions that cause the processor to execute:
a three-dimensional region of interest (ROI) setter configured to establish a three-dimensional ROI on volume data being an aggregate of data acquired from three-dimensional space within a living body, and a projected image generator configured to execute a rendering process on the data within the three-dimensional ROI, and generate a three-dimensional projected image, wherein the three-dimensional ROI setter includes:
an accepting part configured to accept an instruction from a user which includes a start point on a predetermined tomographic image of the volume data, and a clipping plane determiner configured to determine a clipping plane that spatially separates tissue to be imaged and tissue not to be imaged in the three-dimensional ROI, wherein the clipping plane determiner determines a first boundary curve on the tomographic image, the first boundary curve passing the start point and being a path connecting pixels that minimizes a sum of energy values calculated from respective pixel values of the pixels, and determines the clipping plane from the first boundary curve, wherein the clipping plane determiner includes:
an energy map generator configured to divide the tomographic image into two, by a pixel line passing the start point, calculate the energy values of each of the pixels in each of the divided images, and generate respective energy maps therefrom, a path search determiner configured to search for a minimum energy path being a path connecting the pixels that minimize the sum of the energy values in each of the energy maps, and determine divided boundary curves in the respective divided images, and a coupler configured to couple the divided boundary curves and obtain the first boundary curve, and wherein the path search determiner is further configured to calculate a variance of the energy values of at least one path candidate being obtained in searching for the minimum energy path, and assume, as the divided boundary curve, the path candidate with the sum of the energy values being equal to or smaller than a first threshold, and the variance being equal to or smaller than a second threshold.

* * * * *